United States Patent
Zhang

(10) Patent No.: US 11,497,787 B2
(45) Date of Patent: Nov. 15, 2022

(54) FUNCTIONALIZED POLY-ADP-RIBOSE POLYMERS FOR DRUG DELIVERY

(71) Applicant: University of Southern California, Los Angeles, CA (US)

(72) Inventor: Yong Zhang, Los Angeles, CA (US)

(73) Assignee: University of Southern California, Los Angeles, CA (US)

( * ) Notice: Subject to any disclaimer, the term of this patent is extended or adjusted under 35 U.S.C. 154(b) by 0 days.

(21) Appl. No.: 17/599,309

(22) PCT Filed: Mar. 27, 2020

(86) PCT No.: PCT/US2020/025396
§ 371 (c)(1),
(2) Date: Sep. 28, 2021

(87) PCT Pub. No.: WO2020/205592
PCT Pub. Date: Oct. 8, 2020

(65) Prior Publication Data
US 2022/0088112 A1    Mar. 24, 2022

Related U.S. Application Data

(60) Provisional application No. 62/826,808, filed on Mar. 29, 2019.

(51) Int. Cl.
| | |
|---|---|
| A61K 38/07 | (2006.01) |
| A61K 47/54 | (2017.01) |
| A61K 47/68 | (2017.01) |
| A61K 47/64 | (2017.01) |
| A61K 47/60 | (2017.01) |
| A61P 35/00 | (2006.01) |
| A61K 31/537 | (2006.01) |
| A61K 31/704 | (2006.01) |

(52) U.S. Cl.
CPC ............ *A61K 38/07* (2013.01); *A61K 31/537* (2013.01); *A61K 31/704* (2013.01); *A61K 47/548* (2017.08); *A61K 47/549* (2017.08); *A61K 47/60* (2017.08); *A61K 47/64* (2017.08); *A61K 47/6815* (2017.08); *A61K 47/6849* (2017.08); *A61P 35/00* (2018.01)

(58) Field of Classification Search
CPC .. A61K 47/548; A61K 47/6815; A61K 47/64; A61K 47/549; A61K 47/60; A61K 47/6807; A61K 47/6803; A61K 47/56; A61K 47/68
See application file for complete search history.

(56) References Cited

PUBLICATIONS

Wu etal (Molecular Cancer Therapeutics, 2006, vol. 5, pp. 52-59) (Year: 2006).*
Alvarez-Gonzalez et al., "Characterization of Polymers of Adenosine Diphosphate Ribose Generated In Vitro and In Vivo," Biochem., 26(11):3218-3224, Jun. 1987.
Gajria et al., "HER2-Amplified Breast Cancer: Mechanisms of Trastuzumab Resistance and Novel Targeted Therapies," Expert Rev Anticancer Ther., 11(2):263-275, Feb. 2011.
Gibson et al., "New Insights into the Molecular and Cellular Functions of poly(ADP-Ribose) and PARPs," Nat Rev Mol Cell Biol., 13(7):411-424, Jun. 2012.
International Search Report and Written Opinion of the ISA/US in PCT/US2020/025396, dated Jul. 16, 2020 8pgs.
Van Geel et al., "Chemoenzymatic Conjugation of Toxic Payloads to the Globally Conserved N-Glycan of Native mAbs Provides Homogeneous and Highly Efficacious Antibody—Drug Conjugates," Bioconjugate Chem., 26(11):2233-2242, Jun. 2015.
Wallrodt et al., "Investigation of the Action of poly(ADP-Ribose)-Synthesising Enzymes on NAD+ Analogues," Beilstein J Org Chem., 13:495-501, Mar. 2017.
Zarkovic et al., "Characterization of DNA ADP-Ribosyltransferase Activities of PARP2 and PARP3: New Insights into DNA ADP-Ribosylation," Nucleic Acids Res., 46(5):2417-2431, Mar. 2018.
Zhang et al., "A Ribose-Functionalized NAD+ with Unexpected High Activity and Selectivity for Protein Poly-ADP-Ribosylation," Nat Commun., 10(1):4196, Sep. 2019.
Adumeau, et al., Site-Specifically Labeled Antibody—Drug Conjugate for Simultaneous Therapy and ImmunoPET, Mol. Pharmaceutics, 15(3):892-898, Jan. 2018.
Jiang et al., "Clickable NAD Analogues for Labeling Substrate Proteins of Poly(ADP-ribose) Polymerases," J. Am. Chem. Soc., 132(27):9363-9372, Jun. 2010.

* cited by examiner

*Primary Examiner* — Karen A. Canella
(74) *Attorney, Agent, or Firm* — Haukaas Fortius PLLC; Michael Haukaas

(57) ABSTRACT

Novel antibody-drug conjugates (ADCs) and methods of using such ADCs to treat proliferative disorders are described herein. The ADCs may comprise a PARP protein automodified with a plurality of poly-ADP-ribose polymers functionalized with novel NAD+ analogues. The automodified PARP with functionalized poly-ADP-ribose polymers provide a novel type of drug carrier, which allows facile conjugation of monoclonal antibodies and cytotoxic drug in high ratios.

19 Claims, 16 Drawing Sheets

Specification includes a Sequence Listing.

FUNCTIONALIZED POLY-ADP-RIBOSE POLYMERS FOR DRUG DELIVERY

RELATED APPLICATIONS

This application is a National Stage filing under 35 U.S.C. § 371 of International Application No. PCT/US2020/025396 filed Mar. 27, 2020, which claims the benefit of U.S. Provisional Patent Application No. 62/826,808 filed Mar. 29, 2019, which applications are incorporated herein by reference.

SEQUENCE LISTING

The instant application contains a Sequence Listing which has been submitted electronically in ASCII format and is hereby incorporated by reference in its entirety. Said ASCII copy, created on May 18, 2020, is named 530_008WO1_SL.txt and is 1,039 bytes in size.

BACKGROUND OF THE INVENTION

Differentiation and proliferation of biologic cells are normal and ongoing processes that act often in concert to support tissue growth during, for example, cell repair, cell replacement, and organogenesis. The system is tightly regulated to ensure that only appropriate signals are generated based on the needs of the organism. Normally, cell proliferation and differentiation occur only as necessary for the replacement of damaged cells or for growth. However, disruption of these processes may be triggered by many factors including shortage or excess of various signaling molecules, the presence of altered microenvironments, certain genetic mutations, or a combination of these events. Thus, the disruption of normal cellular proliferation and/or differentiation may lead to various disorders including proliferative diseases such as cancer.

Conventional therapeutic treatments for cancer include chemotherapy, radiotherapy, immunotherapy, or in combination. But these treatments often are ineffective and surgical resection may not provide a viable clinical alternative. These limitations in the standard of care particularly are evident in cases where patients undergo first line treatments and subsequently relapse. In such cases, refractory tumors, that often are aggressive and incurable, arise frequently. The overall survival rate for many solid tumors largely have remained unchanged over the years due, in part, to the failure of existing therapies to prevent relapse, tumor recurrence, and metastasis. Therefore, a great need remains still for the development of more targeted and potent therapies for various proliferative disorders.

One such treatment options includes the use of antibody-drug conjugates, or ADCs. These conjugates combine the binding specificity of monoclonal antibodies with the potency of chemotherapeutic agents. The technology associated with the development of monoclonal antibodies to tumor associated target molecules, the use of more effective cytotoxic agents, and the design of chemical linkers to covalently bind these components, has progressed rapidly in recent years. And while various ADCs have shown promise for the treatment of certain proliferative disorders, there remains a need in the art for clinically effective targeted compounds and methods of use of such compounds to treat proliferative disorders. The current invention addresses this need.

SUMMARY

Embodiments of the invention are directed to methods, compounds, antibody-drug conjugates, and pharmaceutical compositions containing antibody-drug conjugates (ADCs), the ADCs comprising an auto-modified poly ADP-ribose polymerase (PARP) as a novel drug carrier. Due to robust automodification activity, human PARP may catalyze the transfer of Adenine Diphosphate-ribose (ADPr) (also known as PARylation) with clickable moieties onto itself, resulting in a plurality of clickable ADPr polymers on the surface of the PARP. The generated automodified PARP with clickable polymers allow conjugation with antibodies, antibody fragments, or other binding proteins, and with cytotoxic agents, to form novel ADCs. The generated ADCs display significant specificity and potency toward targeted cell lines. This versatile platform provides a new class of ADCs with improved efficacy.

Certain embodiments provide an ADC having the general formula of A-L-AMP-D where A is a targeting moiety, L is a linker unit, AMP is an auto-modified PARP, and D is an active agent such as a chemotoxic or diagnostic agent.

In certain embodiments, the targeting moiety is an antibody or an antibody fragment. In certain preferred embodiments, the targeting moiety is a monoclonal antibody. The monoclonal antibody may include, for example, trastuzumab.

The auto-modified PARP is a member of the PARP family. Preferably, the PARP is PARP1 or PARP2. In certain embodiments, the PARP is automodified using a substituted $NAD^+$ analogue. The $NAD^+$ analogue can be substituted with an azido group or an alkyne, for example, an acetylenyl group, a propargyl group, a 1-butynyl group, or a 1-pentynyl group. The substituent can be on a pentosyl hydroxyl group, in place of a pentosyl hydroxyl group (e.g., for an azido group), or on the purine moiety, for example, at the 2-position or on the 6-amino group of the purine. In certain specific embodiments, the substituted $NAD^+$ analogue (modified $NAD^+$ analogue) is 3'-azido $NAD^+$, 3'-alkyne $NAD^+$, 6-alkyne-$NAD^+$ (6-a-$NAD^+$), or 2-alkyne-$NAD^+$ (2-a-$NAD^+$).

The active agent may be a cytotoxic drug, such as a cytotoxic drug effective to treat breast cancer, multiple myeloma, or lymphoma. The breast cancer may be, for example, HER2-positive metastatic breast cancer. In various embodiments, the cytotoxic drug is auristatin, calicheamicin, maytansine or analogues thereof. In certain preferred embodiments, the cytotoxic drug is auristatin, monomethyl auristatin F (MMAF), monomethylauristatin-E (MMAE), or PF-06380101. In alternative embodiments, the active agent is a diagnostic agent comprising a fluorescent contrasting agent, a radiolabel, or an enzymatic moiety.

The automodified PARP may be linked to the targeting moiety and the active through an alkyne, or a polyethylene glycol linking group. Preferably, the linker may undergo a "click chemistry" reaction with the ADPr (having an azido or alkyne group, for example, the 3'-azido $NAD^+$ or 3'-alkyne $NAD^+$) polymer on the surface of the PARP. In one embodiment, the linker connecting the ADPr polymer on the auto-modified PARP to the targeting moiety comprises bicyclo[6.1.0]nonyne (BCN).

One preferred embodiment is a pharmaceutical composition comprising a modified PARP having a plurality of poly ADPr groups on the surface of the PARP, the ribose moiety of the ADPr modified at the 3'-position with an azido group or an alkyne group or at substitutable positions of the purine moiety with an azido group or an alkyne group, a targeting moiety, an active agent, and a pharmaceutically acceptable carrier.

The ratio of auto-modified PARP to the active agent in the composition can be about 1:10 to about 1:100. In some embodiments, the ratio of auto-modified PARP to the active agent can be about 1 to about 20, about 1 to about 50, or about 1 to about 100. The invention also provides a method of treating cancer comprising administering to a subject having cancer or is suspected of having cancer a therapeutically effective amount of an ADC or a composition described herein, thereby inhibiting the growth of cancer cells or killing cancer cells.

Embodiments of the invention also provide a method of preparing a pharmaceutical composition comprising combining a linker and a targeting moiety to provide an antibody-linker conjugate, combining a PARP and a substituted dinucleotide comprising a modified $NAD^+$ analogue to provide an automodified PARP, combining the automodified PARP, the antibody-linker conjugate, and active agent to provide an ADC and a pharmaceutically acceptable carrier. In preferred embodiments, the substituted dinucleotide includes 3'-azido $NAD^+$ or 3'-alkyne $NAD^+$, and more preferably, 3'-azido $NAD^+$.

BRIEF DESCRIPTION OF THE DRAWINGS

The following drawings form part of the specification and are included to further demonstrate certain embodiments or various aspects of the invention. In some instances, embodiments can be best understood by referring to the accompanying drawings in combination with the detailed description presented herein. The description and accompanying drawings may highlight a certain specific example, or a certain aspect of the invention. However, one skilled in the art will understand that portions of the example or aspect may be used in combination with other examples or aspects of the invention.

DETAILED DESCRIPTION

Figure 1:
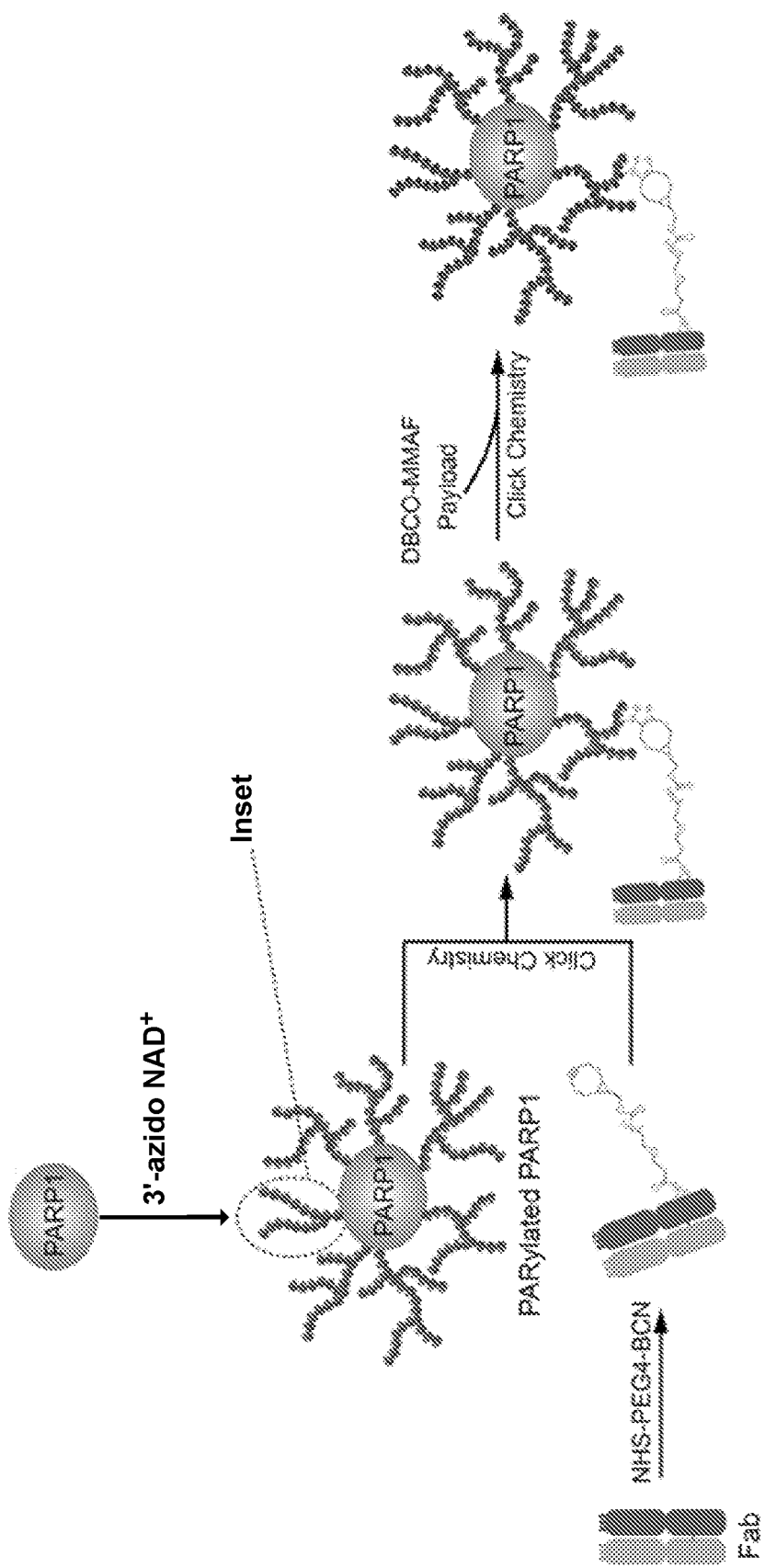
FIG. 1 illustrates a schematic of the design and generation of a poly-ADP-ribose polymer-based antibody-drug conjugate.
Figure 1:
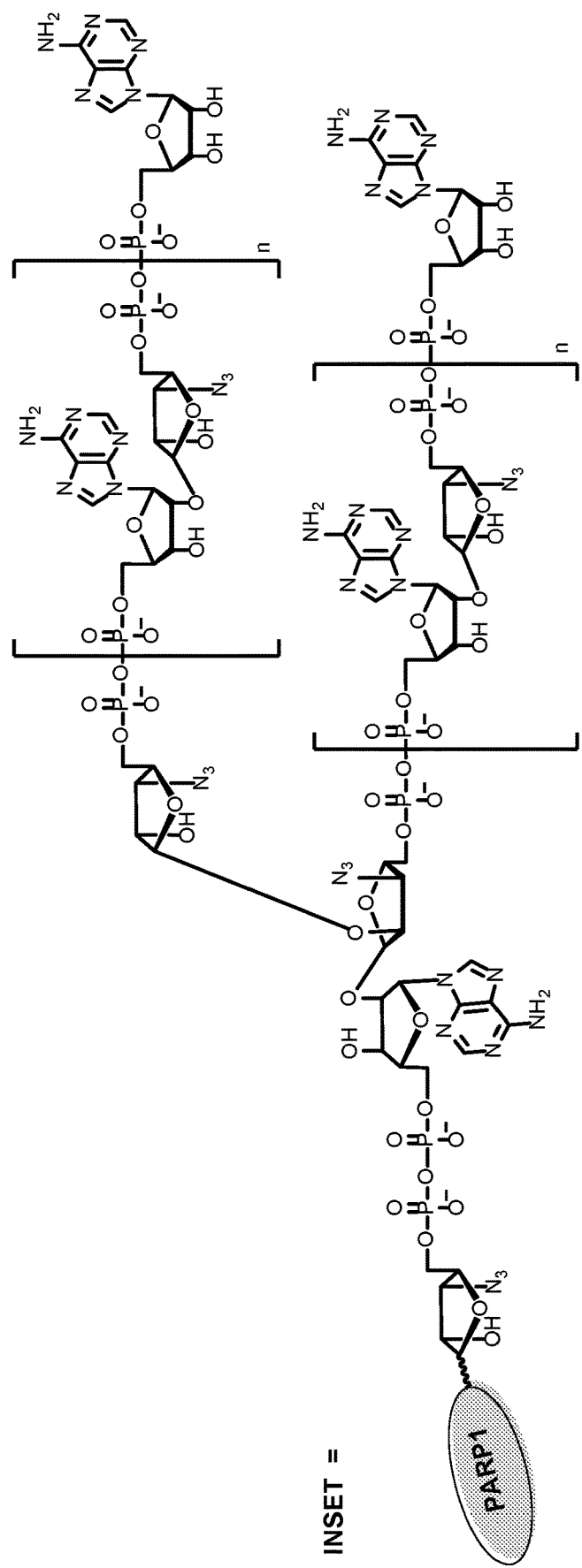
Figure 1:
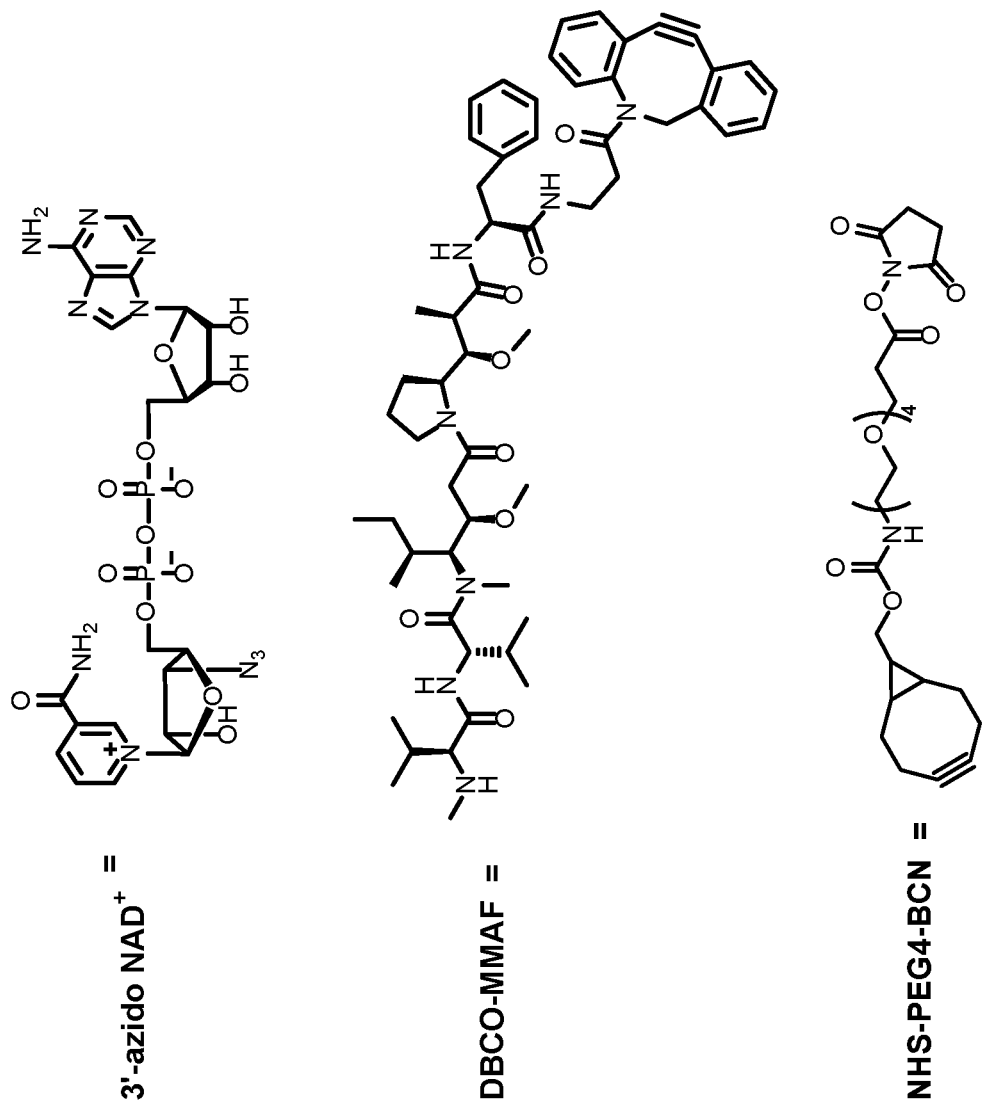

The present disclosure is directed to pharmaceutical compositions and methods for treating malignancies, such as cancers, comprising administering an antibody-drug conjugate having the general formula A-L-AMP-D where A is an antibody or antibody fragment, L is a linker unit, AMP is an automodified PARP comprising a plurality of ADPr polymers, each of the ADPrs having a substituted $NAD^+$ analogue, and D is an active agent such as a chemotoxic or diagnostic agent. Certain embodiments of the disclosure also provide for methods of making the conjugates and pharmaceutical compositions containing the conjugates.

Definitions

The following definitions are included to provide a clear and consistent understanding of the specification and claims. As used herein, the recited terms have the following meanings. All other terms and phrases used in this specification have their ordinary meanings as one of skill in the art would understand. Such ordinary meanings may be obtained by reference to technical dictionaries, such as *Hawley's Condensed Chemical Dictionary* $14^{th}$ Edition, by R. J. Lewis, John Wiley & Sons, New York, N.Y., 2001.

References in the specification to "one embodiment", "an embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect or connect such aspect, feature, structure, moiety, or characteristic with other embodiments, whether or not explicitly described.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for the use of exclusive terminology, such as "solely," "only," and the like, in connection with any element described herein, and/or the recitation of claim elements or use of "negative" limitations.

The term "and/or" means any one of the items, any combination of the items, or all of the items with which this term is associated. The phrases "one or more" and "at least one" are readily understood by one of skill in the art, particularly when read in context of its usage. For example, the phrase can mean one, two, three, four, five, six, ten, 100, or any upper limit approximately 10, 100, or 1000 times higher than a recited lower limit. For example, one or more substituents on a phenyl ring refers to one to five, or one to four, for example if the phenyl ring is disubstituted.

As will be understood by the skilled artisan, all numbers, including those expressing quantities of ingredients, properties such as molecular weight, reaction conditions, and so forth, are approximations and are understood as being optionally modified in all instances by the term "about." These values can vary depending upon the desired properties sought to be obtained by those skilled in the art utilizing the teachings of the descriptions herein. It is also understood that such values inherently contain variability necessarily resulting from the standard deviations found in their respective testing measurements. When values are expressed as approximations, by use of the antecedent "about," it will be understood that the particular value without the modifier "about" also forms a further aspect.

The term "about" can refer to a variation of ±5%, ±10%, ±20%, or ±25% of the value specified. For example, "about 50" percent can in some embodiments carry a variation from 45 to 55 percent, or as otherwise defined by a particular claim. For integer ranges, the term "about" can include one or two integers greater than and/or less than a recited integer at each end of the range. Unless indicated otherwise herein, the term "about" is intended to include values, e.g., weight percentages, proximate to the recited range that are equivalent in terms of the functionality of the individual ingredient, composition, or embodiment. The term about can also modify the endpoints of a recited range as discussed above in this paragraph.

As will be understood by one skilled in the art, for any and all purposes, particularly in terms of providing a written description, all ranges recited herein also encompass any and all possible sub-ranges and combinations of sub-ranges thereof, as well as the individual values making up the range, particularly integer values. It is therefore understood that each unit between two particular units are also disclosed. For example, if 10 to 15 is disclosed, then 11, 12, 13, and 14 are also disclosed, individually, and as part of a range. A recited range (e.g., weight percentages or carbon groups) includes each specific value, integer, decimal, or identity within the range. Any listed range can be easily recognized as sufficiently describing and enabling the same range being broken down into at least equal halves, thirds, quarters, fifths, or tenths. As a non-limiting example, each range discussed herein can be readily broken down into a lower third, middle third and upper third, etc. As will also be understood by one skilled in the art, all language such as "up to", "at least", "greater than", "less than", "more than", "or more", and the like, include the number recited and such terms refer to ranges that can be subsequently broken down into sub-ranges as discussed above. In the same manner, all ratios recited herein also include all sub-ratios falling within the broader ratio. Accordingly, specific values recited for radicals, substituents, and ranges, are for illustration only; they do not exclude other defined values or other values within defined ranges for radicals and substituents. It will be further understood that the endpoints of each of the ranges are significant both in relation to the other endpoint, and independently of the other endpoint.

One skilled in the art will also readily recognize that where members are grouped together in a common manner, such as in a Markush group, the invention encompasses not only the entire group listed as a whole, but each member of the group individually and all possible subgroups of the main group. Additionally, for all purposes, the invention encompasses not only the main group, but also the main group absent one or more of the group members. The invention therefore envisages the explicit exclusion of any one or more of members of a recited group. Accordingly, provisos may apply to any of the disclosed categories or embodiments whereby any one or more of the recited elements, species, or embodiments, may be excluded from such categories or embodiments, for example, for use in an explicit negative limitation.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo.

An "effective amount" refers to an amount effective to treat a disease, disorder, and/or condition, or to bring about a recited effect. For example, an effective amount can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., that is effective to treat or prevent a disease or disorder, or to treat the symptoms of the disease or disorder, in a host. Thus, an "effective amount" generally means an amount that provides the desired effect. An appropriate "effective" amount in any individual case may be determined using techniques, such as a dose escalation study.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" can extend to prophylaxis and can include prevent, prevention, preventing, lowering, stopping or reversing the progression or severity of the condition or symptoms being treated. As such, the term "treatment" can include medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

PARPs.

Poly-ADP-ribose polymerases (PARPs), also known as ADP-ribosyltransferases (ARTs), are emerging as major effectors of $NAD^+$-mediated signaling in cells. PARPS are a diverse family of at least 17 mammalian enzymes that catalyze the reversible post-translational modification—known as ADP-ribosylation, or PARylation—involving the transfer of ADP-ribose from $NAD^+$ to target proteins. This enzymatic posttranslational modification requires nicotinamide adenine dinucleotide ($NAD^+$) as a donor of ADP-ribose. Upon covalent attachments of ADP-riboses to side chains of various types of amino acid residues, PARPs may continue adding ADP-ribose sequentially at ribosyl 2'-OH positions, resulting in linear or branched poly-ADP-ribose (PAR) polymers with up to 300 ADP-ribose units in length.

In various embodiments, the nicotinamide adenine dinucleotide ($NAD^+$) that acts a donor of ADP-ribose in the automodification and/or PARylation reaction is modified at the 2'-OH ($R^1$ position), the 3'-OH ($R^2$ position) position, the 6-amine position of the purine moiety ($R^3$ position), and/or the 2-position of the purine moiety ($R^4$ position) and may include a chemical group that may undergo "click chemistry". Various embodiments include a modified $NAD^+$ analogue having a "click chemistry" group according to Table 1 below.

TABLE 1

Chemical structures of $NAD^+$ analogues 1-9.

| # | $R^1$ | $R^2$ | $R^3$ | $R^4$ |
|---|---|---|---|---|
| 1: | $R^1 =$ propargyl ether | $R^2 =$ OH | $R^3 =$ H | $R^4 =$ H |
| 2: | $R^1 =$ OH | $R^2 =$ propargyl ether | $R^3 =$ H | $R^4 =$ H |
| 3: | $R^1 =$ pentynyl ether | $R^2 =$ OH | $R^3 =$ H | $R^4 =$ H |
| 4: | $R^1 =$ OH | $R^2 =$ pentynyl ether | $R^3 =$ H | $R^4 =$ H |
| 5: | $R^1 = N_3$ | $R^2 =$ OH | $R^3 =$ H | $R^4 =$ H |
| 6: | $R^1 =$ OH | $R^2 = N_3$ | $R^3 =$ H | $R^4 =$ H |
| 7: | $R^1 =$ azidoethyl ether | $R^2 =$ OH | $R^3 =$ H | $R^4 =$ H |
| 8: | $R^1 =$ OH | $R^2 =$ OH | $R^3 = CH_2-\!\!\equiv$ | $R^4 =$ H |
| 9: | $R^1 =$ OH | $R^2 =$ OH | $R^3 =$ H | $R^4 =$ alkyne |

Various modified $NAD^+$ analogue embodiments include modified $NAD^+$ analogues having an alkyne or azido group, such as those shown above in Table 1, at any of the $R^1$-$R^4$ positions, in any different combination. For example, any of analogues 1-7 may also be substituted with an alkyne at the $R^3$ or $R^4$ positions, and of analogues 8-9 can be substituted at the $R^1$ or $R^2$ positions with an oxygen-linked alkyne or alkyl azido group, or can have an azido group in place of a hydroxyl at the $R^1$ or $R^2$ position. In certain preferred embodiments, the NAD+ analogue comprises a chemical structure of NAD+ analogue 2 ($R^1$=OH, $R^2$=alkyne, e.g., propargyl) or NAD+ analogue 6 ($R^1$=OH, $R^2$=azido), also termed 3'-alkyne and 3'-azido, respectively.

Antibody-Drug Conjugates.

Various embodiments may include one or more targeting moiety conjugated to the modified ADPr polymers (e.g., 3'-azido and 3'-alkyne) on the surface of the PARP protein.

Techniques for preparing monoclonal antibodies against virtually any target antigen are well known in the art. See, for example, Köhler and Milstein, *Nature* 256: 495 (1975), and Coligan et al. (eds.), Current Protocols in Immunology, Vol. 1, pages 2.5.1-2.6.7 (John Wiley & Sons 1991). Briefly, monoclonal antibodies can be obtained by injecting mice with a composition comprising an antigen, removing the spleen to obtain B-lymphocytes, fusing the B-lymphocytes with myeloma cells to produce hybridomas, cloning the hybridomas, selecting positive clones which produce antibodies to the antigen, culturing the clones that produce antibodies to the antigen, and isolating the antibodies from the hybridoma cultures.

MAbs can be isolated and purified from hybridoma cultures by a variety of well-established techniques. Such isolation techniques include affinity chromatography with Protein-A or Protein-G Sepharose, size-exclusion chromatography, and ion-exchange chromatography. See, for example, Coligan at pages 2.7.1-2.7.12 and pages 2.9.1-2.9.3. Also, see Baines et al., Methods in Molecular Biology, Vol. 10, pages 79-104 (The Humana Press, Inc. 1992).

After the initial raising of antibodies to the immunogen, the antibodies can be sequenced and subsequently prepared by recombinant techniques. Humanization and chimerization of murine antibodies and antibody fragments are well known to those skilled in the art, as discussed below.

The skilled artisan will realize that the claimed methods and compositions may utilize any of a wide variety of antibodies known in the art. Antibodies of use may be commercially obtained from a wide variety of known sources. For example, a variety of antibody secreting hybridoma lines are available from the American Type Culture Collection (ATCC, Manassas, Va.). A large number of antibodies against various disease targets, including but not limited to tumor-associated antigens, have been deposited at the ATCC and/or have published variable region sequences and are available for use in the claimed methods and compositions. (See, e.g., U.S. Pat. Nos. 7,312,318; 7,282,567; 7,151,164; 7,074,403; 7,060,802; 7,041,803; 6,949,244; 6,946,129; 6,943,020; 6,939,547; 6,921,645; 6,921,645; 6,921,533; 6,919,433; 6,919,078; 6,916,475; 6,905,681; 6,899,879; 6,893,625; 6,887,468; 6,887,466; 6,884,594; 66,187,287; 6,183,744; 6,129,914; 6,120,767; 6,096,289; 6,077,499; 5,922,302; 5,874,540; and 5,814,440, the Examples section of each of which is incorporated herein by reference.) These are exemplary only and a wide variety of other antibodies and their hybridomas are known in the art. The skilled artisan will realize that antibody sequences or antibody-secreting hybridomas against almost any disease-associated antigen may be obtained by a simple search of the ATCC, NCBI and/or USPTO databases for antibodies against a selected disease-associated target of interest. The antigen binding domains of the cloned antibodies may be amplified, excised, ligated into an expression vector, transfected into an adapted host cell and used for protein production, using standard techniques well known in the art. Isolated antibodies may be conjugated to therapeutic agents, such as camptothecins, using the techniques disclosed herein.

Chimeric and Humanized Antibodies

A chimeric antibody is a recombinant protein in which the variable regions of a human antibody have been replaced by the variable regions of, for example, a mouse antibody, including the complementarity-determining regions (CDRs) of the mouse antibody. Chimeric antibodies exhibit decreased immunogenicity and increased stability when administered to a subject. Methods for constructing chimeric antibodies are well known in the art (e.g., Leung et al., 1994, *Hybridoma* 13:469-476).

A chimeric monoclonal antibody may be humanized by transferring the mouse CDRs from the heavy and light variable chains of the mouse immunoglobulin into the corresponding variable domains of a human antibody. The mouse framework regions (FR) in the chimeric monoclonal antibody are also replaced with human FR sequences. To preserve the stability and antigen specificity of the humanized monoclonal, one or more human FR residues may be replaced by the mouse counterpart residues. Humanized monoclonal antibodies may be used for therapeutic treatment of subjects. Techniques for production of humanized monoclonal antibodies are well known in the art. (See, e.g., Jones et al., 1986, *Nature,* 321:522; Riechmann et al., *Nature,* 1988, 332:323; Verhoeyen et al., 1988, *Science,* 239:1534; Carter et al., 1992, *Proc. Nat'l Acad. Sci. USA,* 89:4285). In another embodiment, an antibody may be a human monoclonal antibody. Such antibodies may be obtained from transgenic mice that have been engineered to produce specific human antibodies in response to antigenic challenge.

Human Antibodies

Methods for producing fully human antibodies using either combinatorial approaches or transgenic animals transformed with human immunoglobulin loci are known in the art (e.g., Mancini et al., 2004, *New Microbiol.* 27:315-28; Conrad and Scheller, 2005, *Comb. Chem. High Throughput Screen.* 8:117-26. Such fully human antibodies are expected to exhibit even fewer side effects than chimeric or humanized antibodies and to function in vivo as essentially endogenous human antibodies. In certain embodiments, the claimed methods and procedures may utilize human antibodies produced by such techniques.

In one alternative, the phage display technique may be used to generate human antibodies (e.g., Dantas-Barbosa et al., 2005, *Genet. Mol. Res.* 4:126-40). Human antibodies may be generated from normal humans or from humans that exhibit a particular disease state, such as cancer (Dantas-Barbosa et al., 2005). The advantage to constructing human antibodies from a diseased individual is that the circulating antibody repertoire may be biased towards antibodies against disease-associated antigens.

In one non-limiting example of this methodology, Dantas-Barbosa et al. (2005) constructed a phage display library of human Fab antibody fragments from osteosarcoma patients. Generally, total RNA was obtained from circulating blood lymphocytes (Id.) Recombinant Fab were cloned from the μ, γ and κ chain antibody repertoires and inserted into a phage display library (Id.) RNAs were converted to cDNAs and used to make Fab cDNA libraries using specific primers against the heavy and light chain immunoglobulin sequences (Marks et al., 1991, *J. Mol. Biol.* 222:581-97, incorporated herein by reference). Library construction was performed according to Andris-Widhopf et al. (2000, In: *Phage Display*

Laboratory Manual, Barbas et al. (eds), 1st edition, Cold Spring Harbor Laboratory Press, Cold Spring Harbor, N.Y. pp. 9.1 to 9.22, incorporated herein by reference). The final Fab fragments were digested with restriction endonucleases and inserted into the bacteriophage genome to make the phage display library. Such libraries may be screened by standard phage display methods. The skilled artisan will realize that this technique is exemplary only and any known method for making and screening human antibodies or antibody fragments by phage display may be utilized.

In another alternative, transgenic animals that have been genetically engineered to produce human antibodies may be used to generate antibodies against essentially any immunogenic target, using standard immunization protocols as discussed above. Methods for obtaining human antibodies from transgenic mice are described by Green et al., *Nature Genet.* 7:13 (1994), Lonberg et al., *Nature* 368:856 (1994), and Taylor et al., *Int. Immun.* 6:579 (1994).

A non-limiting example of such a system is the XENO-MOUSE® (e.g., Green et al., 1999, *J. Immunol. Methods* 231:11-23, incorporated herein by reference) from Abgenix (Fremont, Calif.). In the XENOMOUSE® and similar animals, the mouse antibody genes have been inactivated and replaced by functional human antibody genes, while the remainder of the mouse immune system remains intact.

Production of Antibody Fragments.

Some embodiments of the claimed methods and/or compositions may concern antibody fragments. Such antibody fragments may be obtained, for example, by pepsin or papain digestion of whole antibodies by conventional methods. For example, antibody fragments may be produced by enzymatic cleavage of antibodies with pepsin to provide a 5S fragment denoted F(ab')$_2$. This fragment may be further cleaved using a thiol reducing agent and, optionally, a blocking group for the sulfhydryl groups resulting from cleavage of disulfide linkages, to produce 3.5S Fab' monovalent fragments. Alternatively, an enzymatic cleavage using pepsin produces two monovalent Fab fragments and an Fc fragment. Exemplary methods for producing antibody fragments are disclosed in U.S. Pat. Nos. 4,036,945; 4,331, 647; Nisonoff et al., 1960, Arch. Biochem. Biophys., 89:230; Porter, 1959, Biochem. J., 73:119; Edelman et al., 1967, Methods in Enzymology, page 422 (Academic Press), and Coligan et al. (eds.), 1991, Current Protocols in Immunology, (John Wiley & Sons).

Other methods of cleaving antibodies, such as separation of heavy chains to form monovalent light-heavy chain fragments, further cleavage of fragments or other enzymatic, chemical or genetic techniques also may be used, so long as the fragments bind to the antigen that is recognized by the intact antibody. For example, Fv fragments comprise an association of $V_H$ and $V_L$ chains. This association can be noncovalent, as described in Inbar et al., 1972, *Proc. Nat'l. Acad. Sci. USA,* 69:2659. Alternatively, the variable chains may be linked by an intermolecular disulfide bond or cross-linked by chemicals such as glutaraldehyde. See Sandhu, 1992, *Crit. Rev. Biotech.,* 12:437.

Preferably, the Fv fragments comprise $V_H$ and $V_L$ chains connected by a peptide linker. These single-chain antigen binding proteins (scFv) are prepared by constructing a structural gene comprising DNA sequences encoding the $V_H$ and $V_L$ domains, connected by an oligonucleotides linker sequence. The structural gene is inserted into an expression vector that is subsequently introduced into a host cell, such as *E. coli*. The recombinant host cells synthesize a single polypeptide chain with a linker peptide bridging the two V domains. Methods for producing scFvs are well-known in the art. See Whitlow et al., 1991, *Methods: A Companion to Methods in Enzymology* 2:97; Bird et al., 1988, *Science,* 242:423; U.S. Pat. No. 4,946,778; and Pack et al., 1993, *Bio/Technology,* 11:1271.

Another form of an antibody fragment is a single-domain antibody (dAb), sometimes referred to as a single chain antibody. Techniques for producing single-domain antibodies are well known in the art (see, e.g., Cossins et al., *Protein Expression and Purification,* 2007, 51:253-59; Shuntao et al., *Molec Immunol* 2006, 43:1912-19; Tanha et al., *J. Biol. Chem.* 2001, 276:24774-780). Other types of antibody fragments may comprise one or more complementarity-determining regions (CDRs). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells. See Larrick et al., 1991, *Methods: A Companion to Methods in Enzymology* 2:106; Ritter et al. (eds.), 1995, Monoclonal Antibodies: Production, Engineering and clinical Application, pages 166-179 (Cambridge University Press); Birch et al., (eds.), 1995, Monoclonal Antibodies: Principles and Applications, pages 137-185 (Wiley-Liss, Inc.).

Antibody Variations.

In certain embodiments, the sequences of antibodies, such as the Fc portions of antibodies, may be varied to optimize the physiological characteristics of the conjugates, such as the half-life in serum. Methods of substituting amino acid sequences in proteins are widely known in the art, such as by site-directed mutagenesis (e.g. Sambrook et al., *Molecular Cloning, A laboratory manual,* 2$^{nd}$ Ed, 1989). In preferred embodiments, the variation may involve the addition or removal of one or more glycosylation sites in the Fc sequence (e.g., U.S. Pat. No. 6,254,868, the Examples section of which is incorporated herein by reference). In other preferred embodiments, specific amino acid substitutions in the Fc sequence may be made (e.g., Hornick et al., 2000, *J Nucl Med* 41:355-62; Hinton et al., 2006, *J Immunol* 176:346-56; Petkova et al. 2006, *Int Immunol* 18:1759-69; U.S. Pat. No. 7,217,797; each incorporated herein by reference).

Target Antigens and Exemplary Antibodies.

In a preferred embodiment, antibodies are used that recognize and/or bind to antigens that are expressed at high levels on target cells and that are expressed predominantly or exclusively on diseased cells versus normal tissues. More preferably, the antibodies internalize rapidly following binding. An exemplary rapidly internalizing antibody is the LL1 (anti-CD74) antibody, with a rate of internalization of approximately 8×10$^6$ antibody molecules per cell per day (e.g., Hansen et al., 1996, *Biochem J.* 320:293-300). Thus, a "rapidly internalizing" antibody may be one with an internalization rate of about 1×10$^6$ to about 1×10$^7$ antibody molecules per cell per day. Antibodies of use in the claimed compositions and methods may include MAbs with properties as recited above. Exemplary antibodies of use for therapy of, for example, cancer include but are not limited to LL1 (anti-CD74), LL2 or RFB4 (anti-CD22), veltuzumab (hA20, anti-CD20), rituximab (anti-CD20), obinutuzumab (GA101, anti-CD20), lambrolizumab (anti-PD-1 receptor), nivolumab (anti-PD-1 receptor), ipilimumab (anti-CTLA-4), RS7 (anti-epithelial glycoprotein-1 (EGP-1, also known as TROP-2)), PAM4 or KC4 (both anti-mucin), MN-14 (anti-carcinoembryonic antigen (CEA, also known as CD66e or CEACAMS), MN-15 or MN-3 (anti-CEACAM6), Mu-9 (anti-colon-specific antigen-p), Immu 31 (an anti-alpha-fetoprotein), R1 (anti-IGF-1R), A19 (anti-CD19), TAG-72 (e.g., CC49), Tn, J591 or HuJ591 (anti-PSMA (prostate-specific membrane antigen)), AB-PG1-XG1-026 (anti-PSMA dimer), D2/B (anti-PSMA), G250 (an anti-carbonic anhydrase IX MAb), L243 (anti-HLA-DR) alemtuzumab (anti-CD52), bevacizumab (anti-VEGF), cetuximab (anti-EGFR), gemtuzumab (anti-CD33), ibritumomab tiuxetan (anti-CD20);

panitumumab (anti-EGFR); tositumomab (anti-CD20); PAM4 (aka clivatuzumab, anti-mucin) and trastuzumab (anti-ErbB2). Such antibodies are known in the art (e.g., U.S. Pat. Nos. 5,686,072; 5,874,540; 6,107,090; 6,183,744; 6,306,393; 6,653,104; 6,730.300; 6,899,864; 6,926,893; 6,962,702; 7,074,403; 7,230,084; 7,238,785; 7,238,786; 7,256,004; 7,282,567; 7,300,655; 7,312,318; 7,585,491; 7,612,180; and 7,642,239.)

Other useful antigens that may be targeted using the described conjugates include carbonic anhydrase IX, B7, CCCL19, CCCL21, CSAp, HER-2/neu, BrE3, CD1, CD1a, CD2, CD3, CD4, CD5, CD8, CD11A, CD14, CD15, CD16, CD18, CD19, CD20 (e.g., C2B8, hA20, 1F5 MAbs), CD21, CD22, CD23, CD25, CD29, CD30, CD32b, CD33, CD37, CD38, CD40, CD40L, CD44, CD45, CD46, CD52, CD54, CD55, CD59, CD64, CD67, CD70, CD74, CD79a, CD80, CD83, CD95, CD126, CD133, CD138, CD147, CD154, CEACAMS, CEACAM6, CTLA-4, alpha-fetoprotein (AFP), VEGF (e.g., AVASTIN®, fibronectin splice variant), ED-B fibronectin (e.g., L19), EGP-1 (TROP-2), EGP-2 (e.g., 17-1A), EGF receptor (ErbB1) (e.g., ERBITUX®), ErbB2, ErbB3, Factor H, FHL-1, Flt-3, folate receptor, Ga 733, GRO-$\beta$, HMGB-1, hypoxia inducible factor (HIF), HM1.24, HER-2/neu, insulin-like growth factor (ILGF), IFN-$\gamma$, IFN-$\alpha$, IFN-$\beta$, IL-2R, IL-4R, IL-6R, IL-13R, IL-15R, IL-17R, IL-18R, IL-2, IL-6, IL-8, IL-12, IL-15, IL-17, IL-18, IL-25, IP-10, IGF-1R, Ia, HM1.24, gangliosides, HCG, the HLA-DR antigen to which L243 binds, CD66 antigens, i.e., CD66a-d or a combination thereof, MAGE, mCRP, MCP-1, MIP-1A, MIP-1B, macrophage migration-inhibitory factor (MIF), MUC1, MUC2, MUC3, MUC4, MUC5ac, placental growth factor (P1GF), PSA (prostate-specific antigen), PSMA, PAM4 antigen, PD-1 receptor, NCA-95, NCA-90, A3, A33, Ep-CAM, KS-1, Le(y), mesothelin, MOO, tenascin, TAC, Tn antigen, Thomas-Friedenreich antigens, tumor necrosis antigens, tumor angiogenesis antigens, TNF-$\alpha$, TRAIL receptor (R1 and R2), TROP-2, VEGFR, RANTES, T101, as well as cancer stem cell antigens, complement factors C3, C3a, C3b, C5a, C5, and an oncogene product.

Bispecific and Multispecific Antibodies.

Bispecific antibodies are useful in a number of biomedical applications. For instance, a bispecific antibody with binding sites for a tumor cell surface antigen and for a T-cell surface receptor can direct the lysis of specific tumor cells by T cells. Bispecific antibodies recognizing gliomas and the CD3 epitope on T cells have been successfully used in treating brain tumors in human patients (Nitta, et al. *Lancet.* 1990; 355:368-371). A preferred bispecific antibody is an anti-CD3×anti-CD19 antibody. In alternative embodiments, an anti-CD3 antibody or fragment thereof may be attached to an antibody or fragment against another B-cell associated antigen, such as anti-CD3×anti-CD20, anti-CD3×anti-CD22, anti-CD3×anti-HLA-DR or anti-CD3×anti-CD74. In certain embodiments, the techniques and compositions for therapeutic agent conjugation disclosed herein may be used with bispecific or multispecific antibodies as the targeting moieties.

Numerous methods to produce bispecific or multispecific antibodies are known, as disclosed, for example, in U.S. Pat. No. 7,405,320, the Examples section of which is incorporated herein by reference. Bispecific antibodies can be produced by the quadroma method, which involves the fusion of two different hybridomas, each producing a monoclonal antibody recognizing a different antigenic site (Milstein et al., *Nature,* 1983; 305:537-540).

Another method for producing bispecific antibodies uses heterobifunctional cross-linkers to chemically tether two different monoclonal antibodies (Staerz, et al. Nature, 1985; 314:628-631; Perez, et al. *Nature,* 1985; 316:354-356). Bispecific antibodies can also be produced by reduction of each of two parental monoclonal antibodies to the respective half molecules, which are then mixed and allowed to reoxidize to obtain the hybrid structure (Staerz and Bevan. *Proc Natl Acad Sci USA.* 1986; 83:1453-1457). Another alternative involves chemically cross-linking two or three separately purified Fab' fragments using appropriate linkers. (See, e.g., European Patent Application 0453082).

Other methods include improving the efficiency of generating hybrid hybridomas by gene transfer of distinct selectable markers via retrovirus-derived shuttle vectors into respective parental hybridomas, which are fused subsequently (DeMonte et al. *Proc Natl Acad Sci* USA.

1990, 87:2941-2945); or transfection of a hybridoma cell line with expression plasmids containing the heavy and light chain genes of a different antibody.

Cognate $V_H$ and $V_L$ domains can be joined with a peptide linker of appropriate composition and length (usually consisting of more than 12 amino acid residues) to form a single-chain Fv (scFv) with binding activity. Methods of manufacturing scFvs are disclosed, for example, in U.S. Pat. Nos. 4,946,778 and 5,132,405. Reduction of the peptide linker length to less than 12 amino acid residues prevents pairing of $V_H$ and $V_L$ domains on the same chain and forces pairing of $V_H$ and $V_L$ domains with complementary domains on other chains, resulting in the formation of functional multimers. Polypeptide chains of $V_H$ and $V_L$ domains that are joined with linkers between 3 and 12 amino acid residues form predominantly dimers (termed diabodies). With linkers between 0 and 2 amino acid residues, trimers (termed triabody) and tetramers (termed tetrabody) are favored, but the exact patterns of oligomerization appear to depend on the composition as well as the orientation of V-domains ($V_H$-linker-$V_L$ or $V_L$-linker-$V_H$), in addition to the linker length.

These techniques for producing multispecific or bispecific antibodies exhibit various difficulties in terms of low yield, necessity for purification, low stability or the labor-intensiveness of the technique. More recently, a technique known as "dock and lock" (DNL) has been utilized to produce combinations of virtually any desired antibodies, antibody fragments and other effector molecules (see, e.g., U.S. Pat. Nos. 7,521,056; 7,527,787; 7,534,866; 7,550,143; 7,666, 400; 7,858,070; 7,871,622; 7,906,121; 7,906,118; 8,163, 291; 7,901,680; 7,981,398; 8,003,111 and 8,034,352). The technique utilizes complementary protein binding domains, referred to as anchoring domains (AD) and dimerization and docking domains (DDD), which bind to each other and allow the assembly of complex structures, ranging from dimers, trimers, tetramers, quintamers and hexamers. These form stable complexes in high yield without requirement for extensive purification. The DNL technique allows the assembly of monospecific, bispecific or multispecific antibodies. Any of the techniques known in the art for making bispecific or multispecific antibodies may be utilized in the practice of the presently claimed methods. (see, e.g., U.S. Pat. No. 9,446,123).

In various embodiments, a conjugate as disclosed herein may be part of a composite, multispecific antibody. Such antibodies may contain two or more different antigen binding sites, with differing specificities. The multispecific composite may bind to different epitopes of the same antigen, or alternatively may bind to two different antigens In one embodiment, the antibody is a monoclonal antibody (MAb). In other embodiments, the antibody may be a multivalent and/or multispecific MAb. The antibody may be a murine, chimeric, humanized, or human monoclonal antibody, and said antibody may be in intact, fragment (Fab, Fab', F(ab)$_2$, F(ab')$_2$), or sub-fragment (single-chain constructs) form, or of an IgG1, IgG2a, IgG3, IgG4, IgA isotype, or submolecules therefrom.

In certain preferred embodiments, the targeting moiety is Trastuzumab as disclosed in U.S. Pat. No. 5,821,337. Trastuzumab was the first monoclonal antibody developed for the treatment of HER2-positive breast cancer and has increased survival times for patients so that they are now the same as for patients with HER2-negative breast cancer.

Linker Groups.

In certain embodiments, the linker may include a functional group or moiety that is capable of undergoing a click chemistry reaction. The click chemistry approach was originally conceived as a method to rapidly generate complex substances by joining small subunits together in a modular fashion. (See, e.g., Evans, R A, 2007, *Aust J Chem* 60(6): 384-95.) Multiple variations of click chemistry reaction are known in the art, such as the Huisgen 1,3-dipolar cycloaddition copper catalyzed reaction (Tornoe et al., 2002, *J. Org. Chem.* 67:3057-64). Other alternative reaction mechanisms include cycloaddition reactions such as the Diels-Alder, nucleophilic substitution reactions (especially to small strained rings like epoxy and aziridine compounds), carbonyl chemistry formation of urea compounds and reactions involving carbon-carbon double bonds, such as alkynes in thiol-yne reactions.

The azide alkyne Huisgen cycloaddition reaction uses a copper catalyst in the presence of a reducing agent to catalyze the reaction of a terminal alkyne group attached to a first molecule. In the presence of a second molecule comprising, for example, an azide moiety, the azide reacts with the activated alkyne to form a 1,4-disubstituted 1,2,3-triazole. Advantageously the copper catalyzed reaction occurs at room temperature and is sufficiently specific that purification of the reaction product is often not required (Tornoe et al., 2002, *J. Org. Chem* 67:3057). Advantageously, the azide and alkyne functional groups are largely inert towards biomolecules in aqueous medium, thus permitting the reaction to occur in complex solutions. The resultant triazole is chemically stable and may not be subject to enzymatic cleavage, making the click chemistry product highly stable in biological systems. And although the copper catalyst is toxic to living cells, the copper-based click chemistry reaction may be used in vitro for immunoconjugate formation.

A copper-free click reaction also has been proposed for covalent modification of biomolecules. (See, e.g., Agard et al., *J. Am. Chem. Soc.* 2004, 126, 46, 15046-15047). In this system, the copper-free reaction uses ring strain in place of the copper catalyst to promote a [3+2] azide-alkyne cycloaddition reaction. For example, cyclooctyne is an 8-carbon ring structure comprising an internal alkyne bond. The closed ring structure induces a substantial bond angle defor- mation of the acetylene, which is highly reactive with azide groups to form a triazole. Thus, cyclooctyne derivatives may be used for copper-free click reactions.

Another type of copper-free click reaction (Ning et al, *Angew Chem Int Ed Engl.* 2010 Apr. 12; 49(17): 3065-3068.) is based upon strain-promoted alkyne-nitrone cycloaddition. To address the slow rate of the original cyclooctyne reaction, electron-withdrawing groups are attached adjacent to the triple bond. Examples of such substituted cyclooctynes include difluorinated cyclooctynes, 4-dibenzocyclooctynol and azacyclooctyne. An alternative copper-free reaction involved strain-promoted alkyne-nitrone cycloaddition to give N-alkylated isoxazolines. The reaction was reported to have exceptionally fast reaction kinetics and was used in a one-pot three-step protocol for site-specific modification of peptides and proteins. Nitrones were prepared by the condensation of appropriate aldehydes with N-methylhydroxylamine and the cycloaddition reaction took place in a mixture of acetonitrile and water. These and other known click chemistry reactions may be used to attach carrier moieties to antibodies in vitro.

In some embodiments of the click chemistry reaction, the reactive group comprises an alkyne that is capable of undergoing a 1,3-cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3-cycloaddition reactions with azides in the absence of copper catalysts. Suitable alkynes also include, but are not limited to, substituted alkynes, e.g., fluorinated alkynes, aza-cycloalkynes, bicyclo[6.1.0]nonyne (BCN), and derivatives thereof. Linker-agent comprising such reactive groups are useful for conjugating molecules that have been functionalized with azido groups. Such functionalized molecules may include reactive agents and targeting moieties.

In various embodiments, the linker includes a reaction group capable on undergoing a click chemistry reaction comprising an azide, alkyne, dibenzocyclooctyne, trans-cyclooctene, tetrazine, and bicyclo[16.1.0]nonyne. In one preferred embodiment, the linker is endo-BCN-PEG4-NHS ester. Commercial endo-BCN-PEG4-NHS ester linkers may be used to conjugate the BCN moieties rapidly on to the primary amines of trastuzumab Fab or other antibody or antibody fragment. BCN groups are able to react with azide groups on automodified PARP1 through copper free click chemistry, bridging the targeting group Fab together with automodified PARP1 (Leunissen et al., *Chembioche,* 2014 Jul. 7; 15(10):1446-51).

In certain embodiments, the solubility of the drug may be enhanced by placing a defined polyethyleneglycol (PEG) moiety (i.e., a PEG containing a defined number of monomeric units) between the drug and the antibody, wherein the defined PEG is a low molecular weight PEG, preferably containing 1-30 monomeric units, more preferably containing 1-12 monomeric units.

Active Agents.

One or more active agents are conjugated—preferably via click chemistry as described herein—to the automodified PARP through the plurality of ADPr forming the ADPr polymers on the surface of the PARP. Suitable active agents for use with the invention include, for example, chemotherapeutic drugs such as vinca alkaloids, anthracyclines, epidophyllotoxins, taxanes, antimetabolites, tyrosine kinase inhibitors, alkylating agents, antibiotics, Cox-2 inhibitors, antimitotics, antiangiogenic and proapoptotic agents, particularly doxorubicin, methotrexate, paclitaxel, other camptothecins, and others from these and other classes of anticancer agents, and the like. Other cancer chemotherapeutic drugs include nitrogen mustards, alkyl sulfonates, nitrosoureas, triazenes, folic acid analogs, pyrimidine analogs, purine analogs, platinum coordination complexes, hormones, and the like. Suitable chemotherapeutic agents are described in Remington's Pharmaceutical Sciences, 19th Ed. (Mack Publishing Co. 1995), and in Goodman and Gilman's The Pharmacological Basis of Therapeutics, 7th Ed. (MacMillan Publishing Co. 1985), as well as revised editions of these publications. Other suitable chemotherapeutic agents, such as experimental drugs, are known to those of skill in the art.

Other exemplary active agents include, but are not limited to, 5-fluorouracil, afatinib, aplidin, azaribine, anastrozole, anthracyclines, axitinib, AVL-101, AVL-291, bendamustine, bleomycin, bortezomib, bosutinib, bryostatin-1, busulfan, calicheamycin, camptothecin, carboplatin, 10-hydroxycamptothecin, carmustine, celebrex, chlorambucil, cisplatin (CDDP), Cox-2 inhibitors, irinotecan (CPT-11), SN-38, carboplatin, cladribine, camptothecans, crizotinib, cyclophosphamide, cytarabine, dacarbazine, dasatinib, dinaciclib, docetaxel, dactinomycin, daunorubicin, doxorubicin, 2-pyrrolinodoxorubicine (2P-DOX), cyano-morpholino doxorubicin, doxorubicin glucuronide, epirubicin glucuronide, erlotinib, estramustine, epidophyllotoxin, erlotinib, entinostat, estrogen receptor binding agents, etoposide (VP16), etoposide glucuronide, etoposide phosphate, exemestane, fingolimod, floxuridine (FUdR), 3',5'-O-dioleoyl-FudR (FUdR-dO), fludarabine, flutamide, farnesyl-protein transferase inhibitors, flavopiridol, fostamatinib, ganetespib, GDC-0834, GS-1101, gefitinib, gemcitabine, hydroxyurea, ibrutinib, idarubicin, idelalisib, ifosfamide, imatinib, L-asparaginase, lapatinib, lenolidamide, leucovorin, LFM-A13, lomustine, mechlorethamine, melphalan, mercaptopurine, 6-mercaptopurine, methotrexate, mitoxantrone, mithramycin, mitomycin, mitotane, navelbine, neratinib, nilotinib, nitrosurea, olaparib, plicomycin, procarbazine, paclitaxel, PCI-32765, pentostatin, PSI-341, raloxifene, semustine, sorafenib, streptozocin, SU11248, sunitinib, tamoxifen, temazolomide (an aqueous form of DTIC), transplatinum, thalidomide, thioguanine, thiotepa, teniposide, topotecan, uracil mustard, vatalanib, vinorelbine, vinblastine, vincristine, vinca alkaloids and ZD1839. Such agents may be part of the conjugates described herein or may alternatively be administered in combination with the described conjugates, either prior to, simultaneously with or after the conjugate.

In various embodiments, the active agent is one or more of an auristatin, a tubulysin, a colchicine, a vinca alkaloid, a taxane, a cryptophycin, a maytansinoid, a hemiasterlin, and other tubulin disrupting agents. In various embodiments, the active agent is a taxane such as paclitaxel or docetaxel. In one certain preferred embodiment, the active agent is auristatin, calicheamicin, or maytansine, and more preferably, auristatin. In various embodiments, the auristatin selected from the group consisting of monomethyl auristatin E (MMAE), monomethyl auristatin F (MMAF), and dolostatin-10.

In other embodiments, the active agent may be a diagnostic agent useful for diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions that can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In a preferred embodiment, the antibody binds to an antigen or epitope of an antigen expressed on a cancer or malignant cell, internalized by the cell, and delivers the active agent to the interior of the cell. Examples of cancers treatable by the invention disclosed herein include, but are not limited to, lung cancer, breast cancer, ovarian cancer, cervical cancer, gastrointestinal cancers, head and neck cancer, melanoma, sarcoma, esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm, renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non-small cell lung cancer (NSCLC), squamous cell non-small cell lung cancer, breast cancer, recurrent metastatic breast cancer, hepatocellular carcinoma, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and Sezary syndrome. In one embodiment, the solid tumor is a non-lymphoma solid tumor. In some embodiments, the solid tumor may be multiple myeloma.

Certain embodiments of the invention may bind to healthy cells to deliver the active agent to the interior of the cell for diagnostic or research purposes.

Pharmaceutical Formulations

The compounds described herein can be used to prepare therapeutic pharmaceutical compositions, for example, by combining the compounds with a pharmaceutically acceptable diluent, excipient, or carrier. The compounds may be added to a carrier in the form of a salt or solvate. For example, in cases where compounds are sufficiently basic or acidic to form stable nontoxic acid or base salts, administration of the compounds as salts may be appropriate. Examples of pharmaceutically acceptable salts are organic acid addition salts formed with acids that form a physiologically acceptable anion, for example, tosylate, methanesulfonate, acetate, citrate, malonate, tartrate, succinate, benzoate, ascorbate, a-ketoglutarate, and β-glycerophosphate. Suitable inorganic salts may also be formed, including hydrochloride, halide, sulfate, nitrate, bicarbonate, and carbonate salts.

Pharmaceutically acceptable salts may be obtained using standard procedures well known in the art, for example by reacting a sufficiently basic compound such as an amine with a suitable acid to provide a physiologically acceptable ionic compound. Alkali metal (for example, sodium, potassium or lithium) or alkaline earth metal (for example, calcium) salts of carboxylic acids can also be prepared by analogous methods.

The compounds of the formulas described herein can be formulated as pharmaceutical compositions and administered to a mammalian host, such as a human patient, in a variety of forms. The forms can be specifically adapted to a chosen route of administration, e.g., oral or parenteral administration, by intravenous, intramuscular, topical or subcutaneous routes.

The compounds described herein may be systemically administered in combination with a pharmaceutically acceptable vehicle, such as an inert diluent or an assimilable edible carrier. For oral administration, compounds can be enclosed in hard- or soft-shell gelatin capsules, compressed into tablets, or incorporated directly into the food of a patient's diet. Compounds may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 0.5% to about 60%, about 1% to about 25%, or about 2% to about 10%, of the weight of a given unit dosage form. The amount of active compound in such therapeutically useful compositions can be such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound may be incorporated into sustained-release preparations and devices.

The active compound may be administered intravenously or intraperitoneally by infusion or injection. Solutions of the active compound or its salts can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the active ingredient adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions, or by the use of surfactants. The prevention of the action of microorganisms can be brought about by various antibacterial and/or antifungal agents, for example, parabens, chlorobutanol, phenol, sorbic acid, thimerosal, and the like. In many cases, it will be preferable to include isotonic agents, for example, sugars, buffers, or sodium chloride. Prolonged absorption of the injectable compositions can be brought about by agents delaying absorption, for example, aluminum monostearate and/or gelatin.

Sterile injectable solutions can be prepared by incorporating the active compound in the required amount in the appropriate solvent with various other ingredients enumerated above, as required, optionally followed by filter sterilization. In the case of sterile powders for the preparation of sterile injectable solutions, methods of preparation can include vacuum drying and freeze-drying techniques, which yield a powder of the active ingredient plus any additional desired ingredient present in the solution.

For topical administration, compounds may be applied in pure form, e.g., when they are liquids. However, it will generally be desirable to administer the active agent to the skin as a composition or formulation, for example, in combination with a dermatologically acceptable carrier, which may be a solid, a liquid, a gel, or the like.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which a compound can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user.

Examples of dermatological compositions for delivering active agents to the skin are known to the art; for example, see U.S. Pat. Nos. 4,992,478, 4,820,508, 4,608,392, and 4,559,157. Such dermatological compositions can be used in combinations with the compounds described herein where an ingredient of such compositions can optionally be replaced by a compound described herein, or a compound described herein can be added to the composition.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949. The amount of a compound, or an active salt or derivative thereof, required for use in treatment will vary not only with the particular compound or salt selected but also with the route of administration, the nature of the condition being treated, and the age and condition of the patient, and will be ultimately at the discretion of an attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently formulated in unit dosage form; for example, containing 5 to 1000 mg, conveniently 10 to 750 mg, most conveniently, 50 to 500 mg of active ingredient per unit dosage form. In one embodiment, the invention provides a composition comprising a compound or composition as described herein formulated in such a unit dosage form.

The compound can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

The compounds described herein can be effective anti-tumor agents and have higher potency and/or reduced toxicity as compared to known treatments for AML. Preferably, the compounds employed are more potent and less toxic than known treatments, and/or avoid a potential site of catabolic metabolism encountered with known treatments, i.e., have a different metabolic profile than known treatments.

The invention provides therapeutic methods of treating cancer in a mammal, which involve administering to a mammal having cancer an effective amount of a compound or composition described herein. A mammal includes a primate, human, rodent, canine, feline, bovine, ovine, equine, swine, caprine, bovine and the like.

The ability of a compound or composition described herein to treat cancer may be determined by using assays well known to the art. For example, the design of treatment protocols, toxicity evaluation, data analysis, quantification of tumor cell-kill, and the biological significance of the use of transplantable tumor screens are known. In addition, ability of a compound to treat cancer may be determined using the Tests as described below.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Example 1. Antibody Drug Conjugates (ADCs) Using Automodified PARP1 as a Drug Carrier In response to DNA damage, PARP1 is able to rapidly catalyze the transfer of ADPr units onto itself through a process called automodification, using NAD$^+$ as co-substrates. More than 200 units of ADPr can be added onto each other forming either linear or branched polymer structures on just one acceptor site (FIG. 1). The unique characteristics of PARP1 inspired us to create novel methods using it as a drug carrier, especially in the case of developing novel antibody drug conjugates (ADCs), a class of fast-emerging and promising therapeutics. Cytotoxic agents can be covalently linked to tumor-specific monoclonal antibodies for targeted drug delivery (Lu et al., Int. J. Mol. Sci. 2016, 17, 561). Auristatin, calicheamicin and maytansine are three classes of cytotoxic drugs commonly used in ADCs. The ADCs can efficiently release cytotoxic agents upon entering the targeted tumor cells to reduce the systemic exposure of the body to free drug molecules.

The payload for current ADCs is often limited as they only carry up to 8-12 copies of cytotoxic agents. To rapidly reach therapeutically effective concentrations upon cellular delivery by the linked antibodies, high levels of expression of the tumor antigens, fast internalization rates for antibody carriers, and extremely high potency for the small-molecule chemotherapeutics are required. Such requirements have made it challenging to develop ADCs with desired properties. Cases such that patients develop resistance towards monoclonal antibody treatment due to various cell regulation mechanisms such as autophagy, receptor dimerization and gene mutation become undesirable hurdles impeding drug efficiency. The innovative conjugation approach for attaching small molecule agents onto antibodies with increased drug-to-antibody ratio described herein enables the generation of novel ADCs with significantly enhanced efficacy. The success in generation of such ADCs provides therapies with significant improvement in the therapeutic index of both the antibodies and the cytotoxic agents.

As one of the most widely known and studied monoclonal antibodies, trastuzumab, as well as its ADC trastuzumab-MCC-DM1 (T-DM1), are FDA approved treatments for HER2-positive metastatic breast cancer. Using trastuzumab and T-DM1 as a model, the development of a novel antibody drug conjugate incorporating the auto-PARylation characteristics of PARP1 and click chemistry as conjugation method is described herein. Rapid auto-modification with 3'-azido NAD$^+$ allows PARP1 to transfer multiple ADPr groups containing clickable azide onto itself (FIG. 1). The azide groups on PARP1 can then serve as the linkage spots that are clickable for alkyne groups connected to both the targeting moiety trastuzumab fragment antigen binding (Fab) and the payload Monomethyl auristatin F (MMAF), an anti-tubulin cytotoxic agent inhibiting cell division. Our platform provides an ADC assembly procedure for therapeutic and diagnostic applications as the targeting groups and payload can be changed to target the specific receptors of particular types of cancers.

Auto-PARylated human PARP1 was chosen as model to generate PAR polymers conjugated with targeting moieties and small-molecule drugs because of its strong automodification activity. Anti-HER2 antibody trastuzumab is an approved drug to treat HER2-positive breast cancer. MMAF is a tubulin inhibitor broadly used in antibody-drug conjugates. Trastuzumab was selected as a model targeting antibody and MMAF was selected as the cytotoxic payload for one of the PAR polymer-based antibody-drug conjugates.

Figure 2:
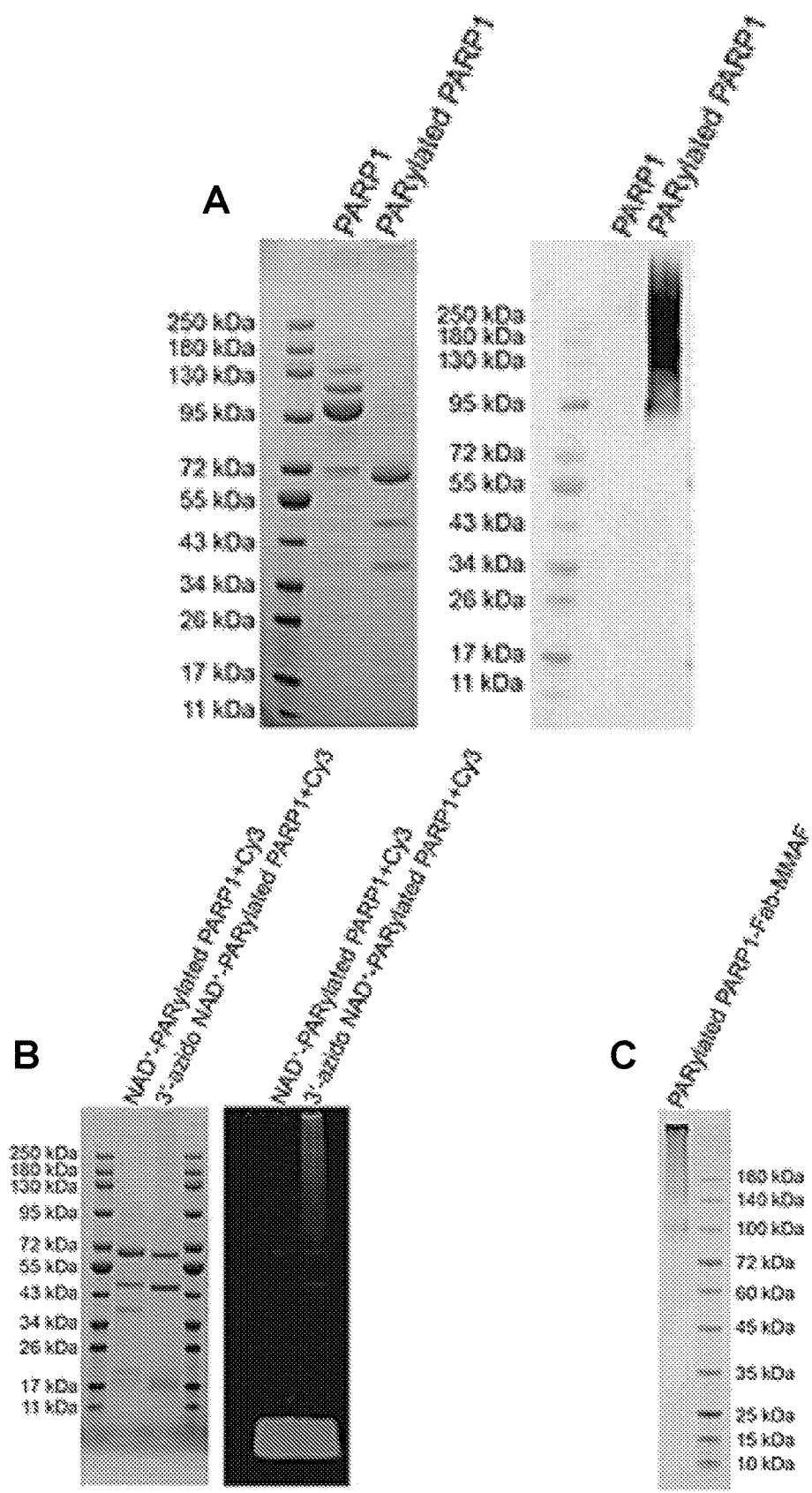
FIG. 2 illustrates the generation and characterization of PARylated PARP1 conjugates. (A) Unmodified PARP1 and PARylated PARP1 by 3'-azido $NAD^+$ as revealed through Coomassie stain (left) and immunoblotting (right) using an anti-PAR antibody. (B) Conjugation of Cy3 with PARylated PARP1 by 3'-azido $NAD^+$ as revealed by Coomassie stain (left) and in-gel fluorescence (right). Auto-modified PARP1 by $NAD^+$ or 3'-azido $NAD^+$ was incubated with DBCO-Cy3 overnight at room temperature, followed by SDS-PAGE in-gel fluorescence and Coomassie stain. (C) Coomassie stain of PARylated PARP1-Fab-MMAF conjugate. (D) Flow cytometric analysis of binding of PARylated PARP1-Fab-Cy3 conjugate to HER2-positive HCC 1954 and HER2-negative MDA-MB-468 cells. PARylated PARP1-Cy3 conjugate (20 ug/mL) was used as a control. (E) Confocal microscopic imaging of internalization of PARylated PARP1-Fab-Cy3 conjugate. HCC 1954 cells (HER2+) were incubated with PARylated PARP1-Fab-Cy3 conjugate (16 µg $mL^{-1}$) in the absence (left) or presence (right) of trastuzumab Fab (800 nM) for 4 hours at 37° C., followed by PBS washes, fixation, DAPI staining, and confocal imaging. Scale bars: 20 µm.
Figure 2:
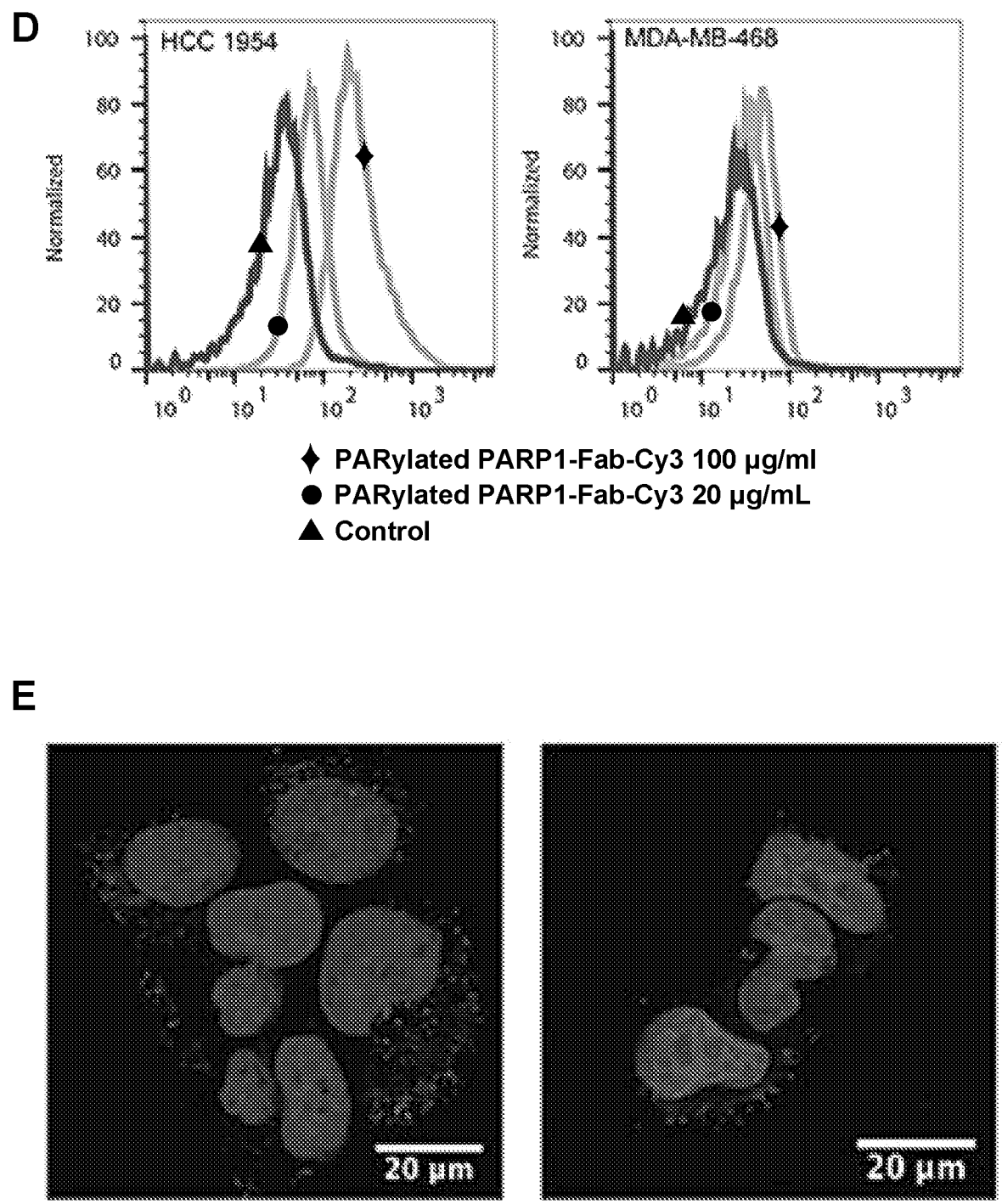

Full-length human PARP1 and the antigen-binding fragment (Fab) of trastuzumab were expressed and purified from *Escherichia coli* (FIG. 5A). PARP1 auto-poly-ADP-ribosylated (PARylated) by 3'-azido $NAD^+$ was then prepared (FIG. 1). PARP1 can be modified by 3'-azido $NAD^+$-derived PAR polymers, which reaction was confirmed by Coomassie stain and immunoblotting (FIG. 2A). Dibenzocyclooctyne (DBCO)-Cy3 fluorescent dye was incubated with PARylated PARP1 by 3'-azido $NAD^+$-to verify the generation of azido-functionalized PAR polymers. In-gel fluorescence imaging revealed fluorescently labeled PAR polymers for PARP1 automodified by 3'-azido $NAD^+$ (FIG. 2B).

Figure 5:
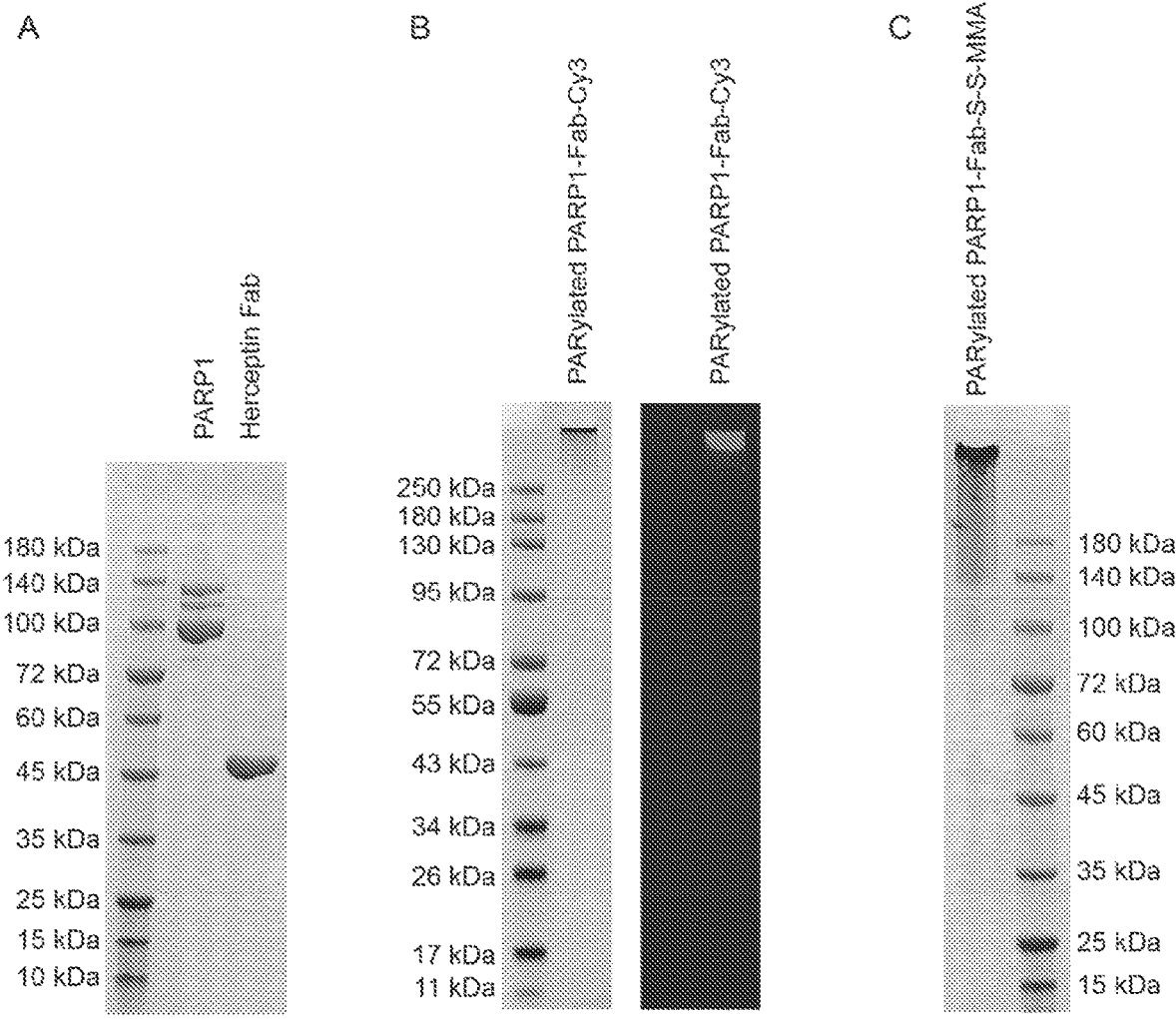
FIG. 5 illustrates an SDS-PAGE analysis of purified proteins and conjugates. (A) Coomassie stain of purified human PARP1 and Herceptin Fab. (B) Coomassie stain (left) and in-gel fluorescence (right) of PARylated PARP1-Fab-Cy3 conjugate. (C) Coomassie stain of PARylated PARP1-Fab-S-S-MMAF conjugate.
Figure 6:
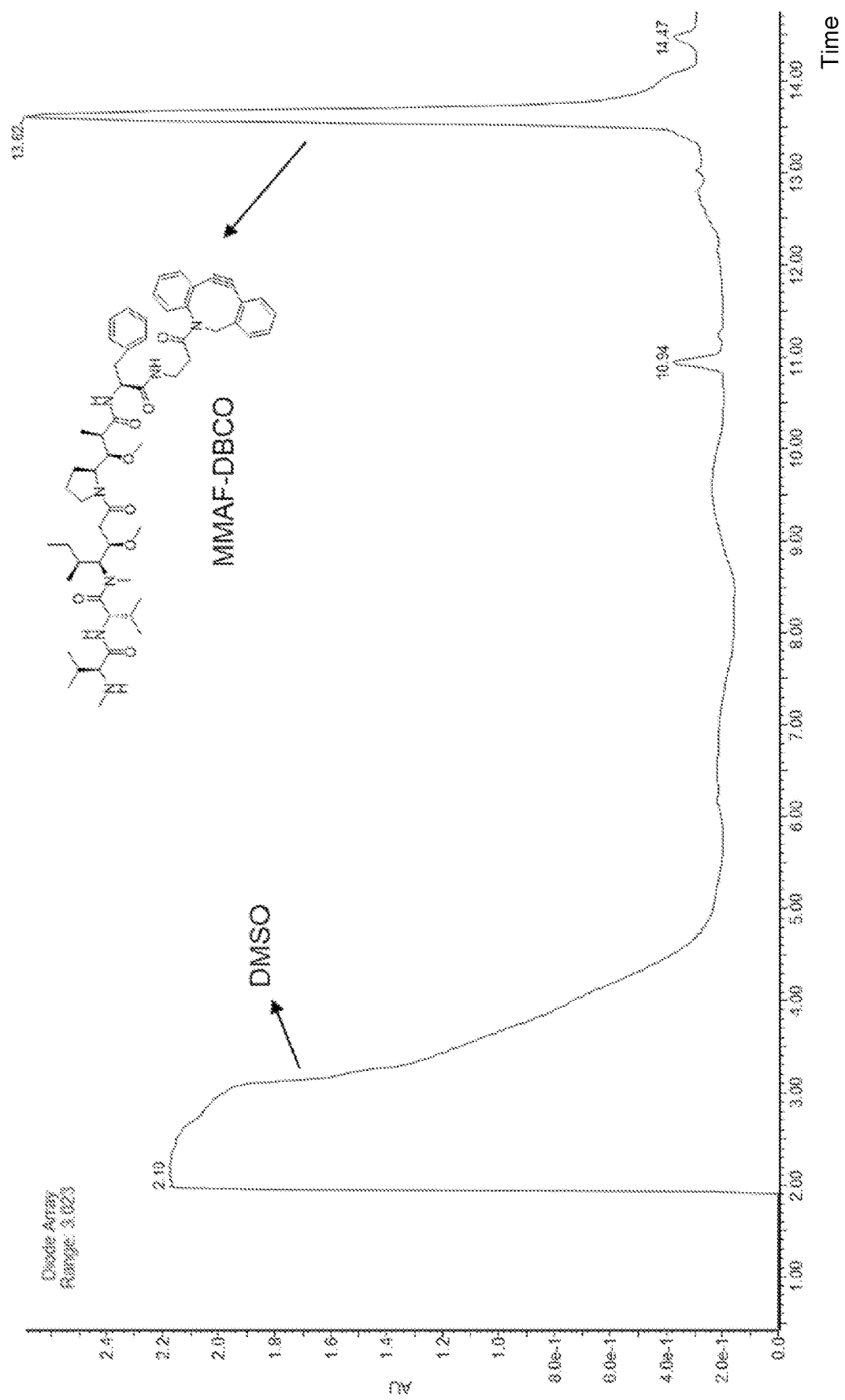
FIG. 6 illustrates an HPLC analysis of DBCO-MMAF molecule.
Figure 7:
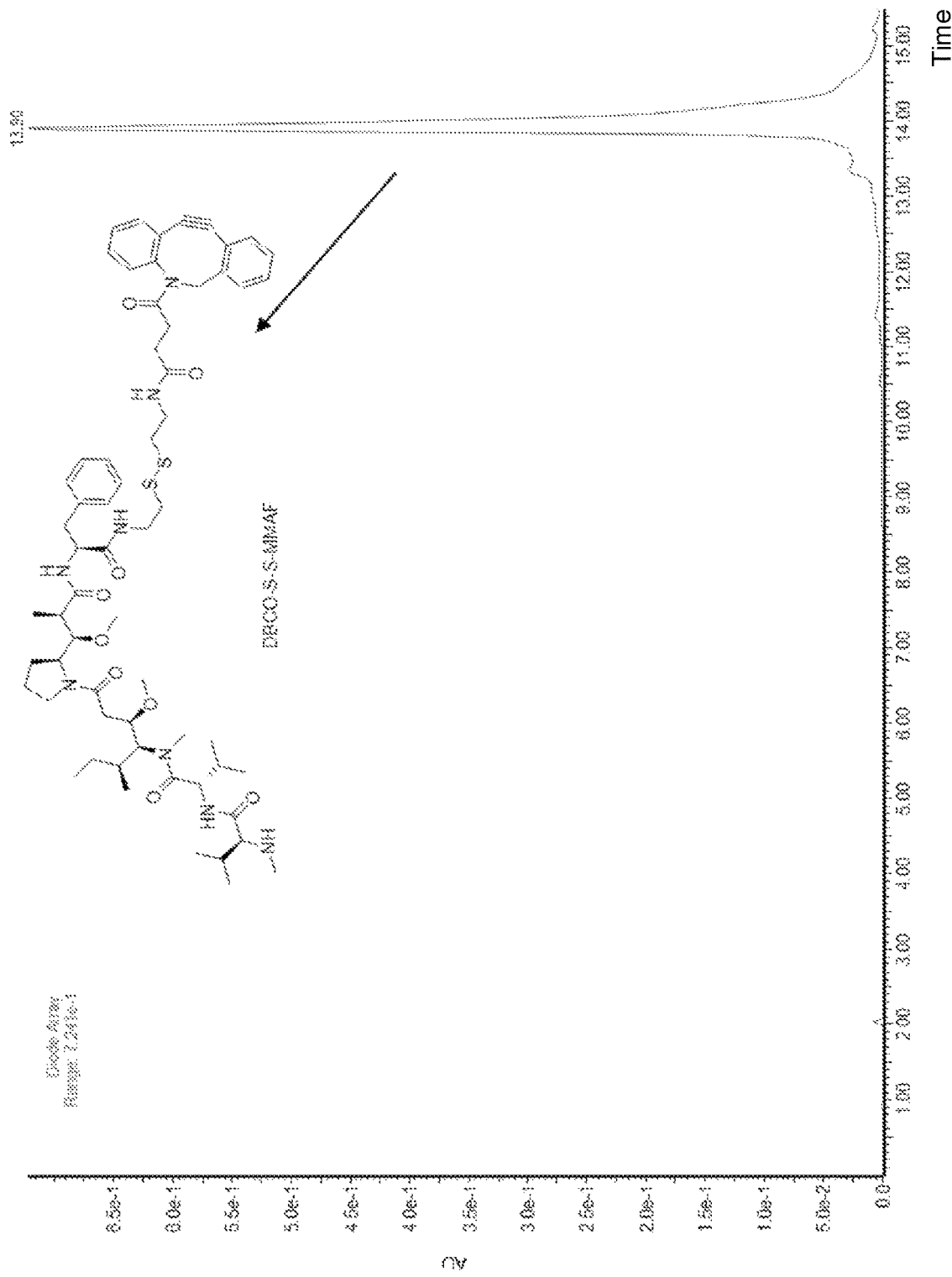
FIG. 7 illustrates an HPLC analysis of the DBCO-S-S-MMAF molecule.
Figure 8:
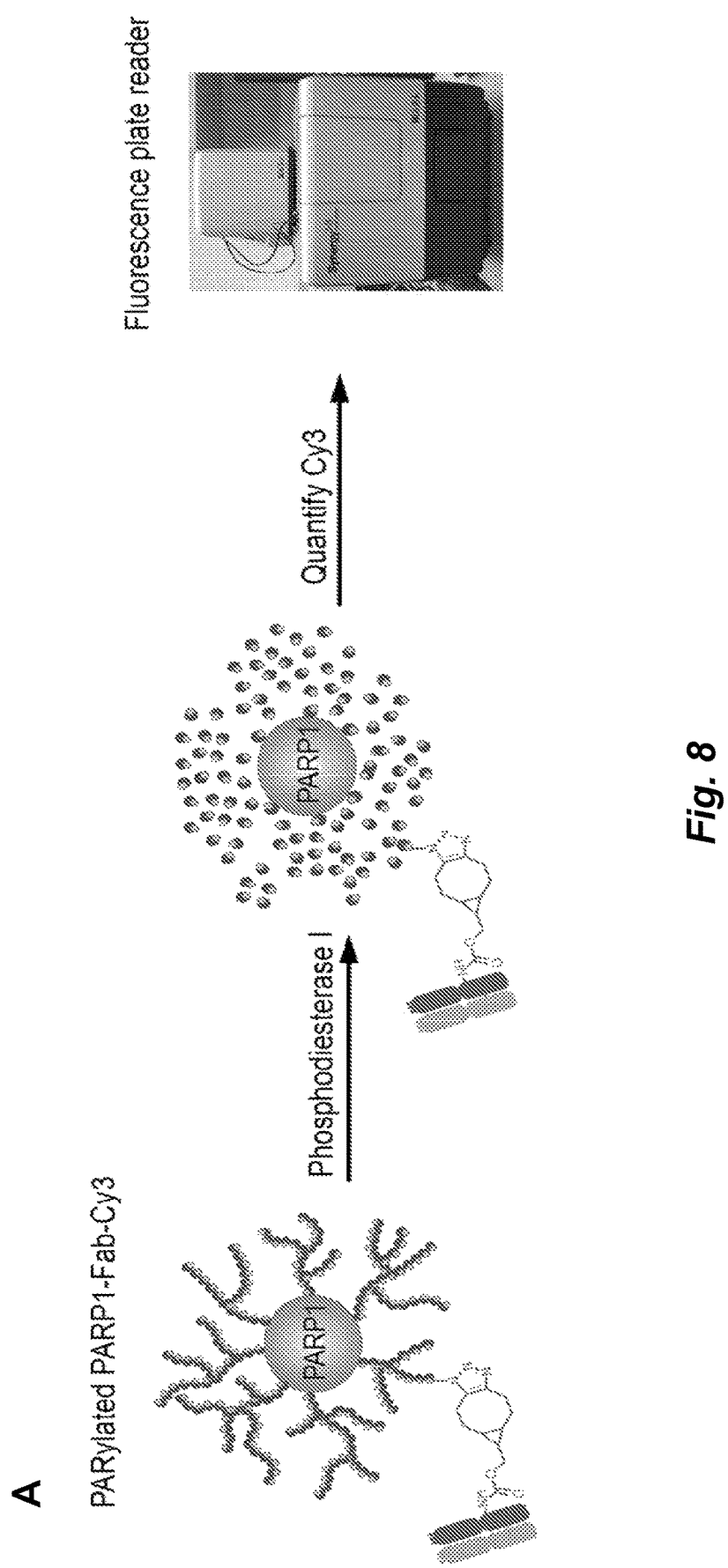
FIG. 8 illustrates a schematic of quantification of the active agent payloads of PARylated PARP1-Fab conjugates. (A) PARylated PARP1-Fab-Cy3 conjugate was treated with phosphodiesterase I to release Cy3 for quantification by a fluorescence plate reader. (B) PARylated PARP1-Fab-S-S-MMAF conjugate was reduced with dithiothreitol (DTT) to release free MMAF-SH for quantification by HPLC.
Figure 8:
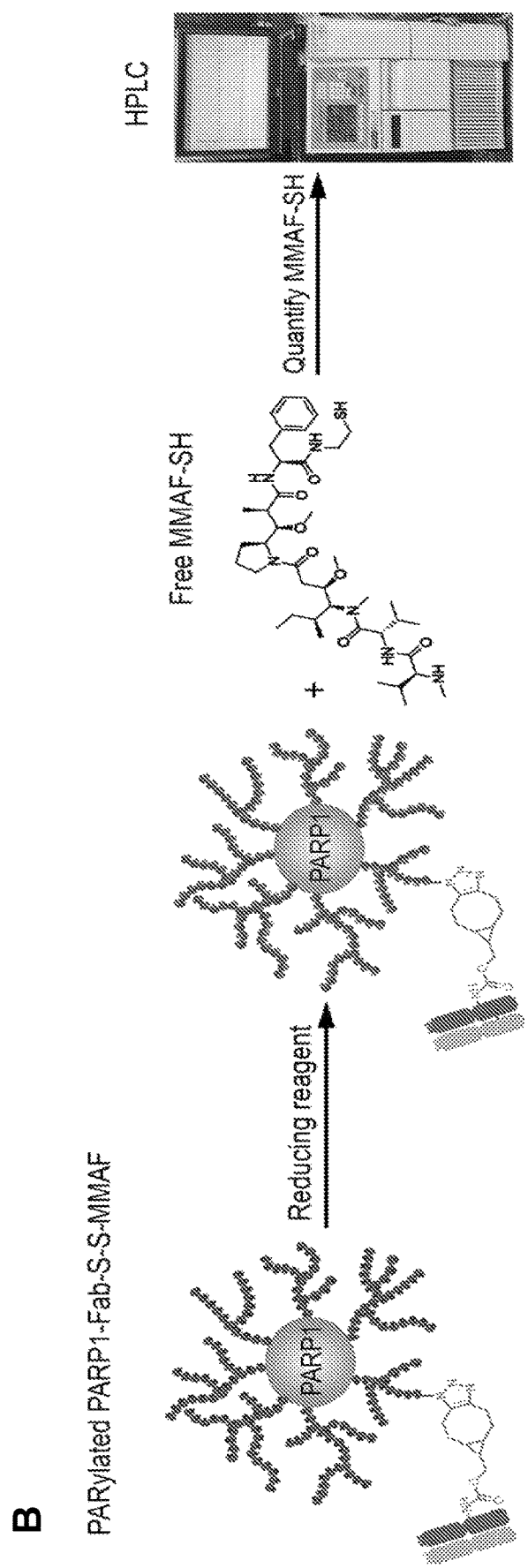

Trastuzumab Fab functionalized with bicyclo[6.1.0]nonyne (BCN) was incubated with 3'-azido $NAD^+$-PARylated PARP1 to synthesize PARylated PARP1-Fab conjugates, which were then conjugation with the prepared DBCO-Cy3 or DBCO-MMAF (see FIG. 6). The PARylated PARP1-Fab-Cy3 and PARylated PARP1-Fab-MMAF conjugates were then purified by gel filtration column (FIG. 5). A DBCO-MMAF conjugate with a disulfide bond in the linker region (DBCO-S-S-MMAF) was also prepared for generating PARylated PARP1-Fab-S-S-MMAF conjugate using the same conditions (FIGS. 5C and 7). The conjugate allowed the release of conjugated MMAF payloads by reducing reagents for quantification purpose.

The binding of PARylated PARP1-Fab-Cy3 conjugate to HER2 receptor was evaluated by flow cytometry with HER2-expressing HCC 1954 and HER2-negative MDA-MB-468 cells (FIG. 2D). It was shown that PARylated PARP1-Fab-Cy3 conjugate could bind to HCC 1954 cells dose dependently but revealed no binding to MDA-MB-468 cells. In addition, confocal microscopic analysis was performed to examine cellular uptake of PARylated PARP1-Fab-Cy3 conjugate (FIG. 2E). By incubating HCC 1954 cells with PARylated PARP1-Fab-Cy3 conjugate without and with trastuzumab Fab at 37° C., confocal imaging indicated internalization of PARylated PARP1-Fab-Cy3 conjugate in a trastuzumab-sensitive manner.

Figure 3:
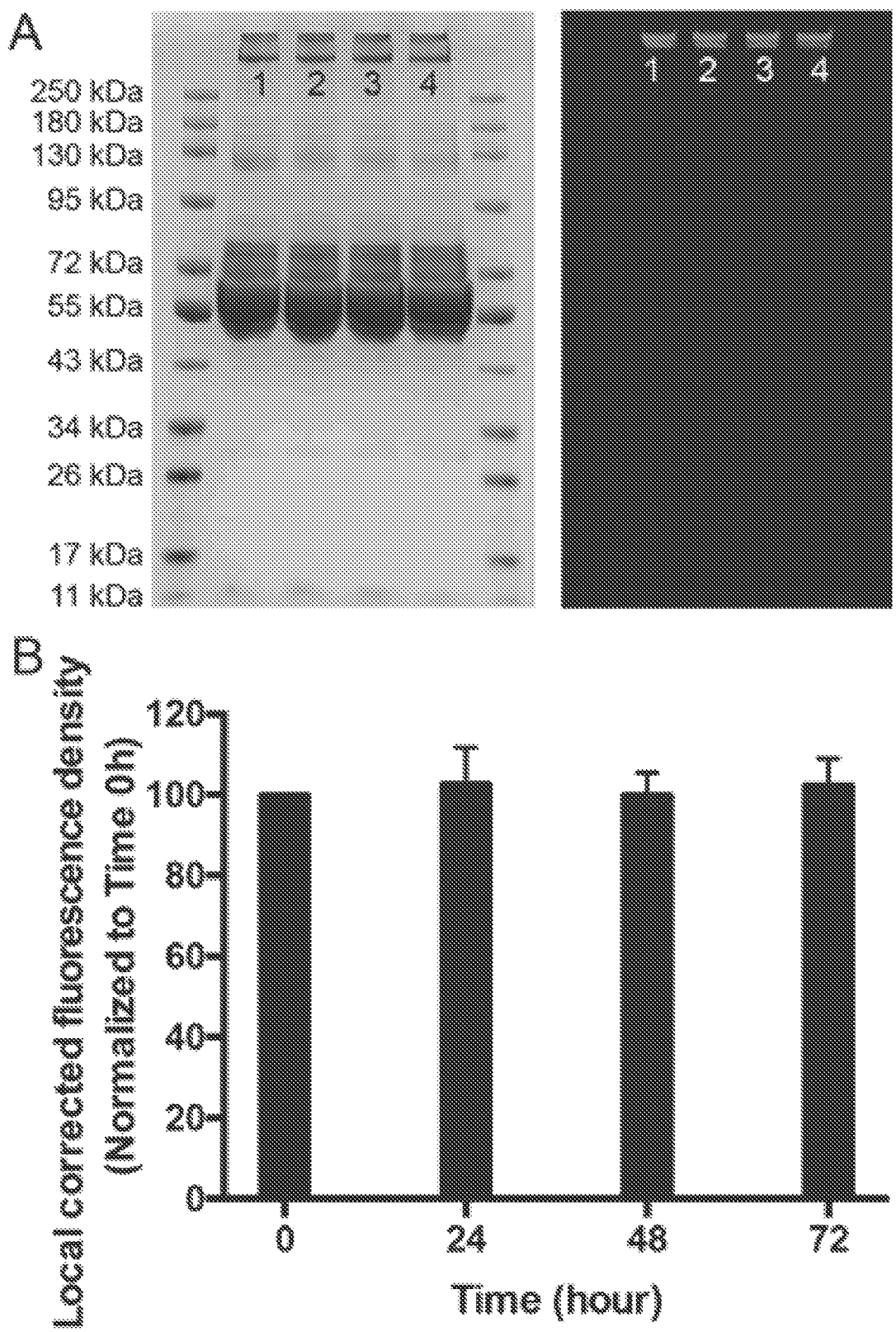
FIG. 3 illustrates the stability of PARylated PARP1-Fab-Cy3 conjugate in culture media. PARylated PARP1-Fab-Cy3 conjugate was diluted with RPMI 1640 medium with 10% FBS, incubated at 37° C. for various amounts of hours, and then analyzed for in-gel fluorescence intensity. (A) Coomassie stain and in-gel fluorescence of PARylated PARP1-Fab-Cy3 conjugate. Lanes 1-4: PARylated PARP1-Fab-Cy3 conjugate incubated in culture media for 0, 24, 48, and 72 h. (B) Quantitative analysis of relative fluorescence intensities of PARylated PARP1-Fab-Cy3 conjugate incubated in culture media for 0-72 h. Data are shown as mean±SD (n=6)

Assessment of the stability of PARylated PARP1-Fab-Cy3 conjugate in cell culture media was performed (FIG. 3) by incubating PARylated PARP1-Fab-Cy3 conjugate diluted in RPMI 1640 medium with 10% fetal bovine serum (FBS) for up to 72 hours at 37° C. No significant changes in the pattern and fluorescence intensity for the PARylated PARP1-Fab-Cy3 conjugate across various time points were indicated by in-gel fluorescence analysis, indicating that PAR polymer-based conjugates are stable in cell culture media and their ability to stably attach drugs for targeted delivery.

Figure 4:
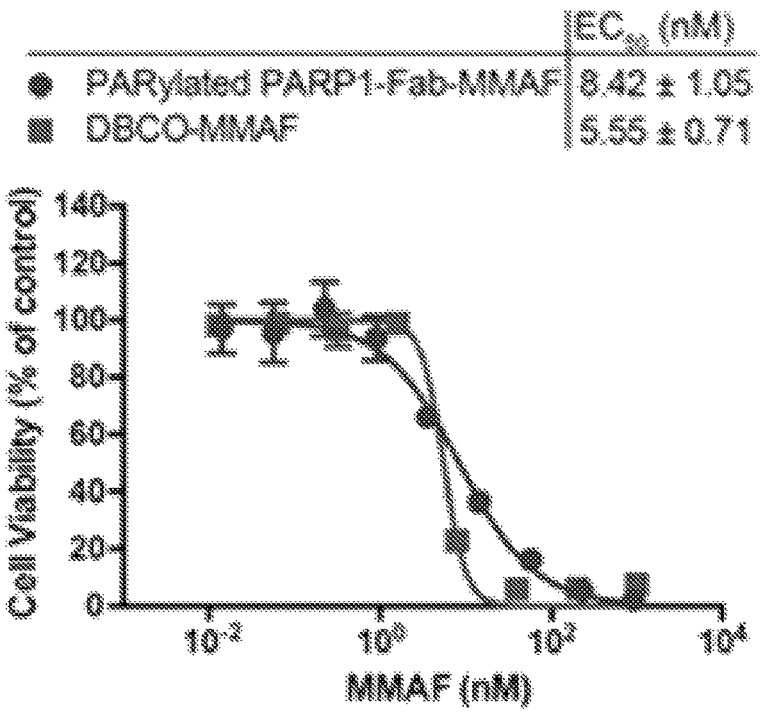
FIG. 4 illustrates an in vitro cytotoxicity of PARylated PARP1-Fab-MMAF conjugate. HCC 1954 (HER2+) and MDA-MB-468 (HER2−) cells were incubated for 72 hours at 37° C. with 5% CO2 in the presence of various concentrations of PARylated PARP1-Fab-MMAF conjugate or DBCO-MMAF (A) and (B) or PARylated PARP1 or PARylated PARP1-Fab conjugate (C) and (D). Cell viability was then measured by MTT assays. Data are shown as mean±SD of duplicates.
Figure 4:
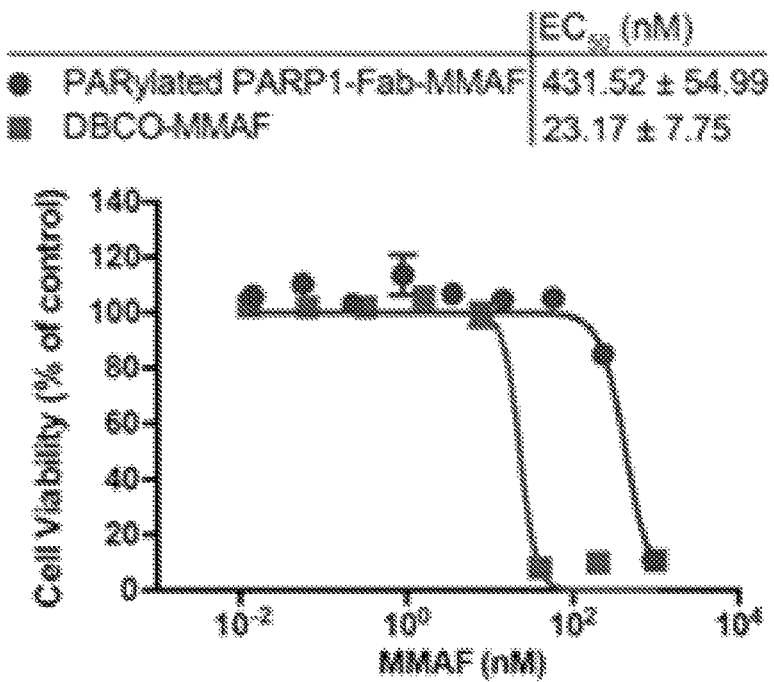
Figure 4:
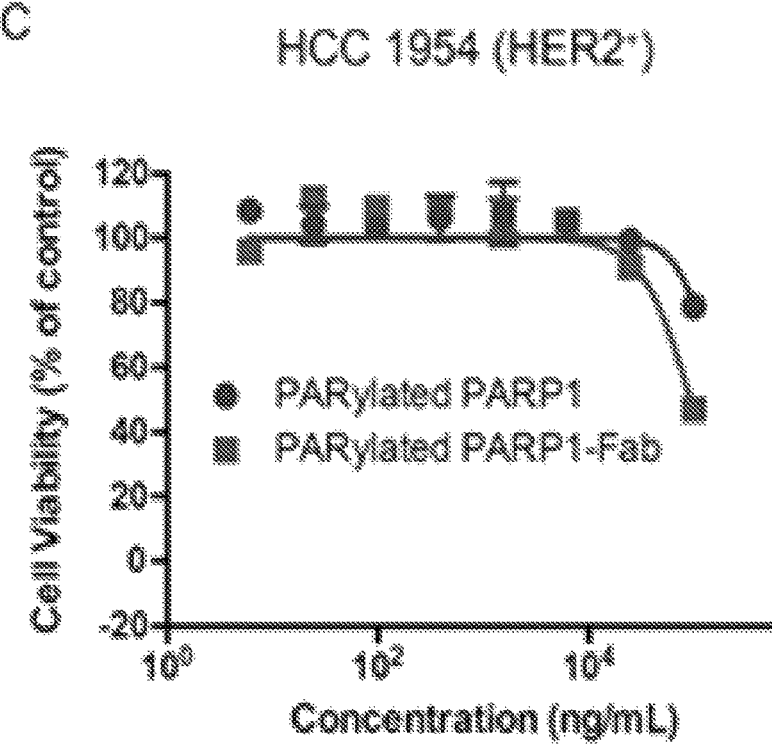
Figure 4:
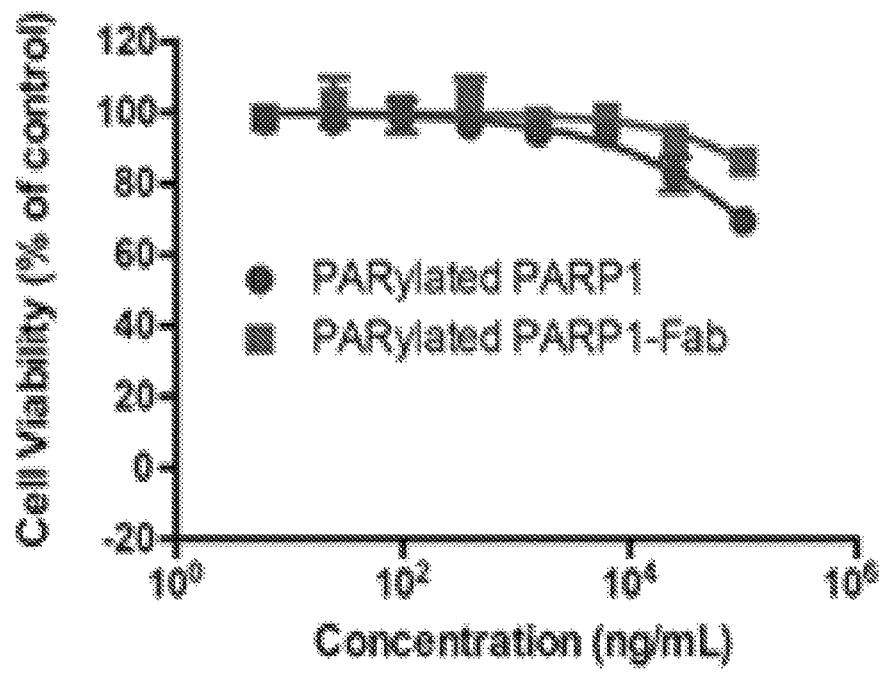
Figure 9:
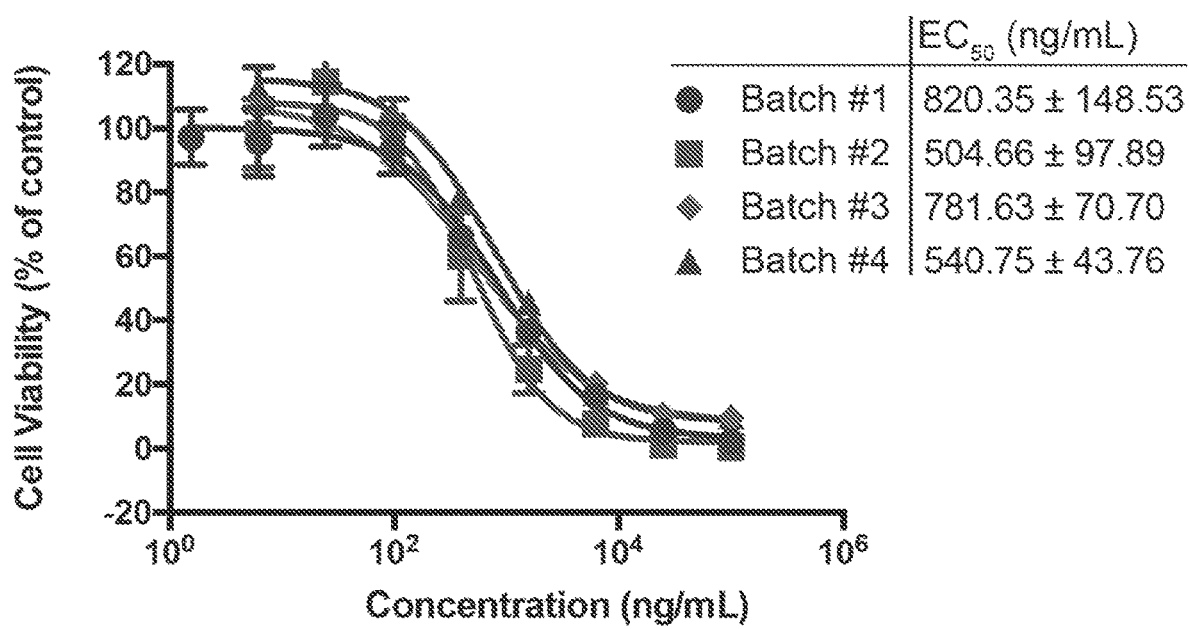
FIG. 9 illustrates in vitro cytotoxicity of PARylated PARP1-Fab-MMAF conjugate for HCC 1954 ($HER2^+$) cells. Cells were incubated for 72 hours at 37° C. with 5% $CO_2$ in the presence of various concentrations of PARylated PARP1-Fab-MMAF conjugates that were prepared with different batches of PARP1 and 3'-azido $NAD^+$. Cell viability was then measured by MTT assays. Data are shown as mean±SD of duplicates.

By treating PARylated PARP1-Fab-Cy3 and PARylated PARP1-Fab-S-S-MMAF with phosphodiesterase I and dithiothreitol (DTT), the released Cy3 and MMAF molecules were quantified to estimate the amounts of conjugated payloads. HCC 1954 and MDA-MB-468 cells were used for in vitro cytotoxicity assays (FIG. 4). It was shown that the PARylated PARP1-Fab-MMAF conjugate showed potent cytotoxicity ($EC_{50}$=8.42 nM) for HER2-expressing HCC 1954 cells, comparable to that of free DBCO-MMAF. The DBCO-MMAF has an $EC_{50}$ of 23.17 nM for MDA-MB-468 cells. In comparison, the potency of PARylated PARP1-Fab-MMAF conjugate for this HER2-negative cell line ($EC_{50}$=431.52 nM) was significantly decreased. As controls PARylated PARP1 and PARylated PARP1-Fab conjugates showed minimal cytotoxicity for both cell lines. In addition, PARylated PARP1-Fab-MMAF conjugates were synthesized through four separate batches and examined for cytotoxicity. The results showed that the conjugated prepared from different batches have consistent cytotoxicity for HER2-expressing HCC 1954 cells (FIG. 9). Taken together, the potency and specificity of PARylated PARP1-Fab-MMAF conjugate in killing HER2-expressing breast cancer cells is demonstrated by these results.

In summary, these results demonstrate that PARylated PARP1-Fab-MMAF conjugate could be successfully generated using the model trastuzumab Fab and MMAF payload. The designed conjugate exhibits potent and specific cytotoxicity toward HER2-expressing cancer cells. The functionalized PAR polymer-based ADC thus represents a novel platform for generating therapeutics with enhanced physicochemical and pharmacological properties compared to established systems for targeted drug delivery.

Cell Lines. Breast cancer cell lines (HCC1954, MDA-MB-468, SK-BR-3 and MDA-MB-231) were obtained from the American Type Culture Collection (ATCC) (Manassas, Va.) and maintained in RPMI 1640 medium supplemented with 10% FBS at 37° C. in 5% $CO_2$.

Figure 10:
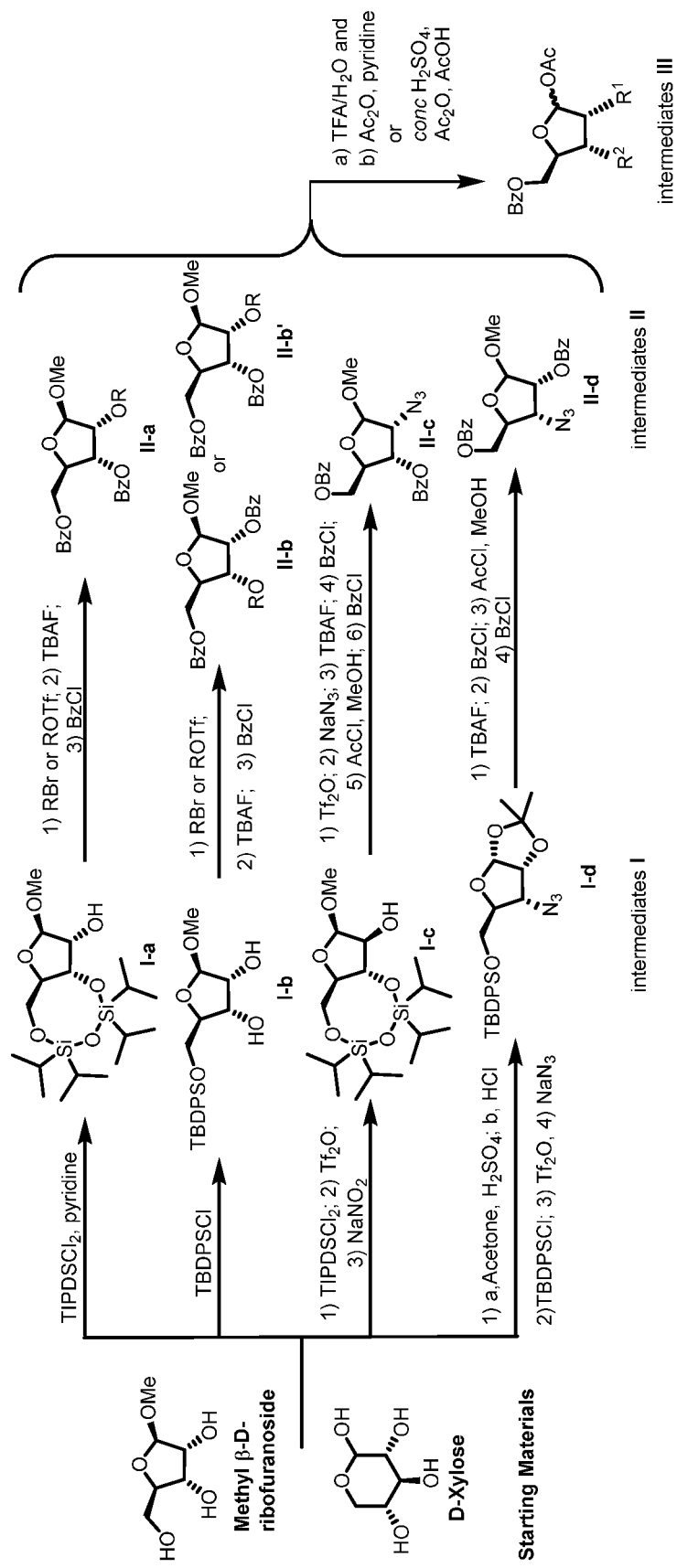
FIG. 10 illustrates the chemical synthesis of $NAD^+$ analogues 1-6.
Figure 10:
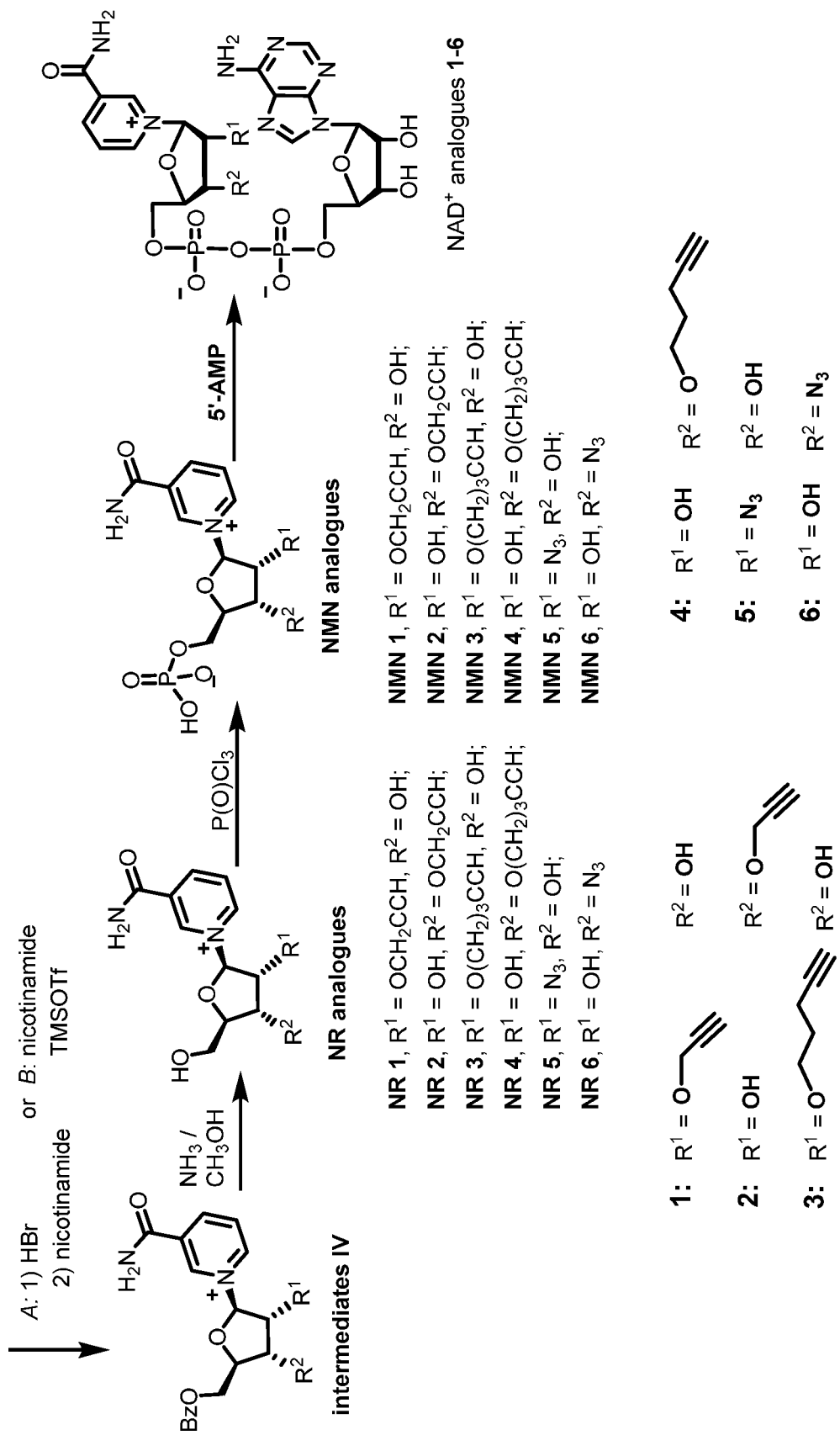

Chemical Synthesis of 3'-azido $NAD^+$. The 3'-azido $NAD^+$ and 3'-alkyne $NAD^+$ ($NAD^+$ analogues 6, and 2, respectively) and other $NAD^+$ analogues disclosed in Table 1 were prepared according to the methods illustrated in FIG. 10 and methods developed by the inventors (see Zhang et al., *Nature communications* 2019, 10 (1), 4196, which is incorporated herein by reference). $NAD^+$ analogues having modified purine moieties can be prepared according to the methods of Du et al. (*Biochemistry* 48, 2878-2890 (2009) (synthesis of 6-alkyne-$NAD^+$ (6-a-$NAD^+$)) and Wang et al. (*Angew. Chem. Int. Ed.* 53, 8159-8162 (2014) (synthesis of 2-alkyne-$NAD^+$ (2-a-$NAD^+$)).

Chemical Synthesis of MMAF-DBCO. To a stirred solution of MMAF (4.4 mg, 0.006 mmol, purchased from Ontario Chemicals, Inc. (Ontario, Canada)), HATU (3.0 mg, 0.0078 mmol, 1.3 eq) and DMAP (0.2 mg, 0.0018 mmol, 0.3 eq) in DMF (0.5 mL) was added with a solution of DBCO-amine (8.3 mg, 0.03 mmol, 5 eq, purchased from Click Chemistry Tools (Scottsdale, Ariz.)) and DIPEA (3 μL, 0.018 mmol, 3 eq) in DMF (0.5 mL) at 0° C. Then, the reaction mixture was allowed to warm to room temperature and stirred at the same temperature until the reaction completed (monitored by HPLC). The reaction was concentrated in vacuo and purified via preparative HPLC (C18-A column, 150×10.0 mm, 5 μm) (mobile phase A: 0.1% formic acid (aq), mobile B: 0.1% formic acid in acetonitrile; flow rate=2.0 mL/min; 0-2 min: 0-4% B, 2-4 min: 4-10% B, 4-6 min: 10-20% B, 6-12 min: 20-50% B, 12-14 min: 50-70% B, 14-16 min: 70-0% B) with detection of UV absorbance at 220 nm. Fractions containing the desired product were concentrated and lyophilized to yield the compound MMAF-DBCO (3.0 mg, 51%) as a colorless solid. MS (ESI) for $C_{57}H_{80}N_7O_8^+$ $(M+H)^+$ Calculated: 990.6068 Da, Observed: 990.6093 Da.

Chemical Synthesis of MMAF-S-S-DBCO. To a stirred solution of MMAF (4.4 mg, 0.006 mmol, purchased from Ontario Chemicals, Inc), HATU (3.0 mg, 0.0078 mmol, 1.3 eq) and DMAP (0.2 mg, 0.0018 mmol, 0.3 eq) in DMF (0.5 mL) was added with a solution of DBCO-S-S-amine (13.2 mg, 0.03 mmol, 5 eq, purchased from Conju-Probe, LLC (San Diego, Calif.)) and DIPEA (3 μL, 0.018 mmol, 3 eq) in DMF (0.5 mL) at 0° C. Then, the reaction mixture was allowed to warm to room temperature and stirred at the same temperature until the reaction completed (monitored by HPLC). The reaction was concentrated in vacuo and purified via preparative HPLC (C18-A column, 150×4.60 mm, 5 μm) (mobile phase A: 0.1% formic acid (aq), mobile B: 0.1% formic acid in acetonitrile; flow rate=1.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 260 nm. Fractions containing the desired product were concentrated and lyophilized to yield the compound MMAF-S-S-DBCO (1.9 mg, 28%) as a colorless solid. MS (ESI) for $C_{62}H_{88}N_8O_9S_2Na^+$ $(M+Na)^+$ Calculated: 1175.6013 Da, Observed: 1175.6029 Da.

Molecular Cloning. Full-length human PARP1 with a C-terminal $His_6$ tag (SEQ ID NO: 3) was amplified through PCR using primers P1 and P2 (Table 2). The amplified DNA fragment was digested by XhoI and XbaI restriction enzymes and then ligated into pET-28a (+) using T4 DNA ligase. All generated expression vectors were confirmed by DNA sequencing provided by Genewiz LLC (South Plainfield, N.J.).

TABLE 2

List of primers used for molecular cloning of full-length human PARP1

| | |
|---|---|
| PARP1-F (SEQ ID NO. 1) | TGGTGCTCGAGCCACAGGGAGGTCTTAAAATTGAA TTTCAGT |
| PARP1-R (SEQ ID NO. 2) | CCCTCTAGAAATAATTTTGTTTAACTTTAAGAAGG AGATATACCATGGCGGAGTCTTCGGATAAGC |

Protein Expression and Purification. The bacterial expression and purification of PARP1 were carried out by according to the following protocols. First, the plasmid of pET-28a (+)-PARP1 was transformed into BL21 (DE3) cells. A single colony was picked and inoculated into 60 mL of LB Broth media with kanamycin (50 μg mL$^{-1}$) for overnight growth at 37° C. in an incubator shaker at a speed of 250 rpm (Series 25, New Brunswick Scientific, N.J.). The overnight bacterial culture was then diluted into six 1-liter LB Broth media with kanamycin (50 μg mL$^{-1}$) for continued growth at 37° C. in an incubator shaker (250 rpm). When the $OD_{600}$ reached 0.6-0.8, 100 mM $ZnSO_4$ was added to the bacterial culture for a final concentration of 0.1 mM. Once the $OD_{600}$ reached 0.8-1.0, the bacterial culture was chilled on ice for 1 hour. Protein expression was then induced with 0.5 mM isopropyl β-D-1-thiogalactopyranoside (IPTG) for overnight at 16° C.

Bacterial cells were harvested by centrifugation at 4,550×g for 50 minutes at 4° C., resuspended in equilibrium buffer (25 mM HEPES pH 8.0, 500 mM NaCl, 1 mM phenylmethylsulfonyl fluoride (PMSF)), and lysed using a French Press (GlenMills, N.J.) at 25,000 psi for three cycles. Cell debris was removed by centrifugation at 27,000×g for 100 minutes at 4° C. and supernatants were filtered through 0.45 μm membranes. The filtrate was loaded on a gravity flow column packed with 5 mL of Ni-NTA agarose resin (Thermo Fisher Scientific, Waltham, Mass.), followed by washing with 50 mL of low-salt wash buffer (25 mM HEPES pH 8.0, 500 mM NaCl, 20 mM imidazole), 50 mL of high-salt wash buffer (25 mM HEPES pH 8.0, 1 M NaCl, 20 mM imidazole) and 50 mL of low-salt wash buffer. Proteins were then eluted with 25 mL of elution buffer (25 mM HEPES pH 8.0, 500 mM NaCl, 400 mM imidazole), followed by addition of 25 mL of no-salt buffer (50 mM Tris pH 7.0, 1 mM EDTA, 0.1 mM dithiothreitol (DTT)). The eluted protein was then loaded onto a 5-mL HiTrap Heparin HP Column (GE Healthcare, Princeton, N.J.).

Upon completion of protein loading by a peristaltic pump, the heparin column was placed on an ÄKTA Pure chromatography system to elute PARP1 using a gradient of 0-100% buffer B (50 mM Tris pH 7.0, 1 mM EDTA, 0.1 mM DTT, 1 M NaCl) in buffer A (50 mM Tris pH 7.0, 1 mM EDTA, 0.1 mM DTT, and 250 mM NaCl) at a flow rate of 1 mL min$^{-1}$. PARP1 was eluted starting at 40% buffer B and the collected fractions were combined and concentrated to below 500 μL using Amicon centrifugal filters with 30 kDa cutoff (EMD Millipore, Temecula, Calif.). The concentrated proteins were injected on to a size-exclusion chromatography column Superdex 200 Increase 10/300 GL (GE Healthcare, Princeton, N.J.) and eluted using gel filtration buffer (25 mM HEPES, pH 8.0, 150 mM NaCl, 1 mM EDTA, 0.1 mM DTT). The fractions containing full-length PARP1 were combined, concentrated using Amicon centrifugal filters with 30 kDa cutoff, analyzed by SDS-PAGE, flash frozen using liquid nitrogen, and stored at −80° C.

To express trastuzumab Fab, DH10B cells transformed with the trastuzumab Fab plasmid were inoculated in LB Broth with ampicillin (100 μg mL$^{-1}$). The overnight bacterial culture (5 mL) was then diluted into 1-liter LB Broth with ampicillin (100 μg mL$^{-1}$) for growth at 37° C. in an incubator shaker at speed of 250 rpm (Series 25, New Brunswick Scientific, N.J.). When the $OD_{600}$ reached 0.6-0.8, protein expression was induced with 0.2% L-arabinose for overnight at 22° C. Cells were then harvested by centrifugation at 4,550×g for 50 minutes at 4° C., resuspended in lysis buffer (25 mM Tris-HCl, pH 8.0, 1 mM EDTA, 1 mM PMSF, 20 mg mL$^{-1}$ lysozyme and 20% (w/v) sucrose) for periplasmic protein extraction. Cells were stirred for 20 minutes and vigorously shaken for another 20 minutes. Cell debris was removed by centrifugation at 27,000×g for 1 hour and supernatants were filtered through a 0.45 μm membrane. The Fabs were purified from the filtrates by Protein G chromatography. Specifically, the filtrates were loaded on a gravity flow column packed with 1 mL of Protein G resin (GenScript, Piscataway, N.J.), followed by washing with PBS. Proteins were then eluted with elution buffer (100 mM glycine, pH 2.7), neutralized with 1 M Tris buffer (pH=8.0) at 10:1 ratio, dialyzed in PBS buffer at 4° C. for overnight and another 6 hours in fresh PBS buffer, and concentrated using Amicon centrifugal concentrators (EMD Millipore, Temecula, Calif.) with a 10 kDa cutoff. Purified Fab was analyzed by SDS-PAGE and stored at −80° C.

Trastuzumab Fab NHS-BCN Linker Conjugation. The endo-BCN-PEG4-NHS ester was dissolved in 100% DMSO as a 100 mM stock. A 20-fold molar excess of endo-BCN-PEG4-NHS ester linker was added into trastuzumab Fab in PBS. The solution was mixed gently and allowed to react at room temperature for two hours. The removal of unreacted linker was performed through buffer exchange using Amicon centrifugal concentrator (EMD Millipore, Temecula, Calif.) with a 10 kDa cutoff in PBS buffer, pH=7.4, with a dilution factor over 1,000,000. The antibody-linker conjugate was then aliquoted and flash-frozen in liquid nitrogen for storage at −80° C. Trastuzumab Fab-PARP1-3'-azido $NAD^+$-MMAF conjugates with drug ratios of 1:20, 1:50 and 1:100 were prepared.

PARP1 Automodification. Large scale auto-PARylation of purified PARP1 was performed at 30° C. for 12 hours in 48 individual 150 µL assay solutions containing 30 mM HEPES, pH 8.0, 5 mM $MgCl_2$, 5 mM $CaCl_2$, 1 mM DTT, 100 ng/µL activated DNA, various concentrations of 3'-azido $NAD^+$ (100 µM for 1:20, 250 µM for 1:50, 500 µM for 1:100), and 5 µM purified PARP1 enzyme. The removal of reaction buffer components and unreacted 3'-azido $NAD^+$ was performed through buffer exchange using Amicon centrifugal concentrator (EMD Millipore, Temecula, Calif.) with a 30 kDa cutoff in PBS buffer, pH=7.4. Purified automodified PARP1 was aliquoted and flash-frozen in liquid nitrogen for storage at −80° C.

Conjugation and Purification of ADCs. Trastuzumab Fab-BCN was added into 100 µL of automodified PARP1 solution with a 1.5-fold molar excess. The conjugation was allowed to proceed at room temperature for 72 hours. Chemically modified MMAF with terminal alkyne or DBCO moieties was dissolved in 100% DMSO to reach a stock concentration of 10 mM. DBCO-MMAF was then slowly added to antibody and PARP1 mixture according to the different molar ratio of 1:20, 1:50 and 1:100 (PARylated PARP1:payloads). Alkyne-MMAF was slowly added to the mixture together with CuAAC reaction buffer (2 mM THPTA, 1 mM $CuSO_4$, 100 µM azide-biotin, and 10 mM sodium ascorbate). DBCO-Alexa 488 was dissolved in 100% DMSO to reach a stock concentration of 5 mM and was slowly added to the reaction mixture using a molar ratio of 1:20. The solution was gently mixed and allowed to react at room temperature for an additional 72 hours.

The precipitates were removed by passing the solutions through a 0.22 µm filter and the conjugates were injected on to a size-exclusion chromatography column Superdex 200 Increase 10/300 GL (GE Healthcare, Princeton, N.J.) and eluted using PBS. Purified conjugates were examined by SDS-PAGE and the protein concentration determined using Coomassie Plus (Bradford) assay reagents, then aliquoted and flash-frozen in liquid nitrogen for storage at −80° C.

Nanoparticle Tracking Analysis (NTA). Nanoparticle tracking analysis was conducted to measure the particle concentration and size distribution of the purified Fab-PARP1-3'-azido $NAD^+$-DBCO-MMAF conjugates using Nanosight LM10 (Malvern Instruments, U.K.) according to the manufacturer's instruction.

Flow Cytometry Binding Analysis. The binding of PARylated PARP1-Fab-Cy3 and PARylated PARP1-Cy3 conjugates to HER2-positive cell line HCC 1954 and HER2-negative cell line MDA-MB-468 were evaluated by flow cytometry. Cells were incubated with PARylated PARP1-Cy3 conjugate at 20 µg $mL^{-1}$ and PARylated PARP1-Fab-Cy3 conjugate at 20 µg $mL^{-1}$ and 100 µg $mL^{-1}$ for 30 minutes at 4° C. and washed three times with PBS containing 2% FBS. Samples were analyzed using a Fortessa X20 flow cytometer (BD Biosciences, San Jose, Calif.). Data were processed by FlowJo software (Tree Star Inc., Ashland, Oreg.).

Confocal Imaging of Cellular Uptake of Conjugates. HCC 1954 cells ($3 \times 10^4$) were seeded onto glass cover slips in 24-well cell culture plates and incubated at 37° C. with 5% $CO_2$ overnight. Cells were then treated with 16 µg $mL^{-1}$ of PARylated PARP1-Fab-Cy3 conjugate in the absence or presence of trastuzumab Fab (800 nM) at 37° C. for 3 h. The cells were gently washed three times with PBS, fixed with 4% paraformaldehyde for 20 minutes, and stained with DAPI for 20 minutes. After three more PBS washes, cells were mounted on slides and imaged with a Leica SP8 confocal laser scanning microscope (Leica Microsystems Inc., Buffalo Grove, Ill.) equipped with HC PL APO 63×/1.40 Oil CS2 oil immersion objective lenses using DAPI and rhodamine (for Cy3) filters. Images were processed using the LAS X software (Leica Microsystems Inc., Buffalo Grove, Ill.) and ImageJ.

In vitro Cytotoxicity Assay. HCC 1954 and MDA-MB-468 cells were seeded in 96-well cell culture plates the day prior to the experiments (5,000 cells per well for HCC 1954 and 6,000 cells per well for MDA-MB-468). The cells were treated with various concentrations of PARP1-Fab-MMAF conjugate or DBCO-MMAF for 72 hours. Ten µL of 3-(4, 5-dimethylthiazol-2-yl)-2,5-diphenyltetrazolium bromide (MTT) solution was then added to the wells and incubated for 2 hours at 37° C. Subsequently, 100 µL of lysis buffer (20% SDS in 50% dimethylformamide, 0.5% (v:v) 80% acetic acid, 0.4% (v:v) 1 N HCl, pH 4.7) was added and incubated for 2 hours at 37° C. The absorbance was measured at 570 nm using a BioTek Synergy H1 Hybrid Multi-Mode Microplate reader (BioTek, VT). Cell viability was calculated as:

% Cell Viability=[(absorbance$_{experimental}$−absorbance$_{spontaneous\ average}$)/(absorbance$_{maximum\ viability\ average}$−absorbance$_{spontaneous\ average}$)]×100

Immunoblot analysis. Purified proteins and conjugates (3 µg) were boiled with 100 mM DTT in NuPAGE LDS sample buffer (Thermo Fisher Scientific, MA) at 98° C. for 10 minutes, separated in 4-20% ExpressPlus-PAGE gels (GenScript, Piscataway, N.J.), and then transferred to Immun-Blot PVDF membranes (Bio-Rad Laboratories, Inc., CA) using a Trans-Blot SD Semi-Dry Transfer Cell (Bio-Rad Laboratories, Inc., CA). The membranes were subsequently blocked with 5% non-fat milk in PBST (PBS with 0.1% Tween-20) for 1 hour at room temperature, followed by incubation with appropriate primary antibodies for 1 h at room temperature, which included an anti-pADPr (10H, Santa Cruz Biotechnology, TX) and anti-$His_6$ ("$His_6$" disclosed as SEQ ID NO: 3) (HIS.H8, Thermo Fisher Scientific, MA) monoclonal antibodies. After 1-hour incubation with the secondary anti-mouse IgG-HRP (Thermo Fisher Scientific, MA), the membranes were developed by additions of SuperSignal West Pico PLUS Chemiluminescent Substrate (Thermo Fisher Scientific, MA) and imaged using a ChemiDoc Touch Imaging System (Bio-Rad Laboratories, Inc., CA).

Stability Test of PARylated PARP1-Fab-Cy3 Conjugate. PARylated PARP1-Fab-Cy3 conjugate was diluted with RPMI 1640 medium with 10% FBS to a final concentration of 0.25 mg $mL^{-1}$ and incubated at 37° C. for 0 h, 24 h, 48 h, and 72 h. Collected samples were separated in 4-20% ExpressPlus-PAGE gels (GeneScript, Piscataway, N.J.), and Cy3-derived fluorescence signals were detected using an iBright FL1000 gel imager (Thermo Fisher Scientific, Waltham, Mass.). Fluorescence intensities were quantified by the iBright FL1000 gel imager (Thermo Fisher Scientific, Waltham, Mass.) and normalized to those of samples incubated for 0 h. The experiment was repeated once and three fluorescence measurements were performed for each experiment. Data are shown as mean±SD (n=6).

Quantification of Cy3 on PARylated PARP1-Fab-Cy3 Conjugate. PARylated PARP1-Fab-Cy3 conjugate was treated with 0.4 mg $mL^{-1}$ of phosphodiesterase I (PDE I) (purchased from Worthington Biochemical Corporation, Lakewood, N.J.) at 37° C. overnight. PDE-treated PARylated PARP1-Fab-Cy3 conjugate and DBCO-Cy3 standards were added into black 96-well plates for fluorescence measurements (excitation at 550 nm; emission at 600 nm) using a BioTek Synergy H1 Hybrid Multi-Mode Microplate reader (BioTek, VT). Cy3 concentrations of PARylated PARP1-Fab-Cy3 conjugate were determined on the basis of standard curves.

Quantification of MMAF on PARylated PARP1-Fab-S-S-MMAF Conjugate. PARylated PARP1-Fab-S-S-MMAF conjugate was treated with 50 mM DTT overnight at room temperature to reduce disulfide bonds and to release MMAF-SH from the conjugate. The supernatants of reaction mixtures and MMAF standards were analyzed by reverse-phase HPLC (C18-A column, 150×10.0 mm, 5 μm) (mobile phase A: 0.1% formic acid (aq), mobile B: 0.1% formic acid in acetonitrile; flow rate=1.0 mL/min; 0-2 min: 0-4% B, 2-4 min: 4-10% B, 4-6 min: 10-20% B, 6-12 min: 20-50% B, 12-17 min: 50-100% B, 17-20 min: 100-0% B) with detection of UV absorbance at 220 nm. Peak areas of MMAF were integrated and plotted against the concentrations of MMAF as the standard curves. MMAF concentrations on PARylated PARP1-Fab-S-S-MMAF were determined on the basis of standard curves.

Automodified PARP1 with functionalized PAR polymers displays promising capabilities as a drug carrier with potentially higher levels of payloads than traditional ADCs. Comparing to some of the biocompatible polymers such as dendrimers and dendritic polymers commonly used in drug delivery, our functionalized PAR polymer-based ADC offers several advantages. Its targeting group trastuzumab Fab has high affinity with HER2 receptors, allowing the ADCs to specifically bind to cancer cells with HER2 overexpression. Once internalized into the cells, the payload can be rapidly released by many widely expressed cytosol enzymes such as PARG and phosphodiesterases (PDE) are hydrolases that can recognize poly ADPr chains and cleave them into single ADPr units, releasing the drug molecules in cells. In addition to specificity and potency, our ADCs provide a model for simple assembly of components of ADC through click chemistry, where the targeting groups and payload can be changed to accommodate future experimental needs in both cancer diagnosis and therapeutics.

Example 2. Bioorthogonal NAD$^+$ Analogues

NAD$^+$ analogues may provide a sensitive method for target identification and distinguishing in between the poly PARP substrates. A drawback to these analogues, however, is that they are unable to permeate through the cell membranes and, thus, cannot be used for the imaging and labeling of PARP1 substrates in live cells. Here, we generated bioorthogonal NAD$^+$, which are featured by a novel class of NAD$^+$ analogues with modified ribose moieties, and, in particular, two new NAD$^+$ analogue with PARP1 substrate activity comparable to or slightly less than that of NAD$^+$. These novel NAD$^+$ analogues may provide a new chemical tool for studying PARylation and as use in ADCs.

Molecular Cloning and Protein Expression and Purification. Full-length human PARP1 with a C-terminal His$_6$-tag (SEQ ID NO: 3) was amplified through PCR using primers P1 and P2. The amplified DNA fragment was digested by XhoI and XbaI restriction enzymes and then ligated into pET-28a (+) using T4 DNA ligase. All generated expression vectors were confirmed by DNA sequencing provided by Genewiz LLC (South Plainfield, N.J.).

The bacterial expression and purification of both full-length PARP1 was carried out by following a previously published protocol with slight modifications (Langelier et al., Methods Mol Biol 2011, 780, 209-26.). BL21 (DE3) cells were transformed with the generated PARP1 and mutant constructs for bacterial protein expression in LB Broth supplemented with kanamycin (50 μg mL$^{-1}$). The overnight bacterial culture (40 mL) was diluted into four 1 liter LB Broth with kanamycin (50 μg mL$^{-1}$) for growth at 37° C. in an incubator shaker at a speed of 250 rpm (Series 25, New Brunswick Scientific, N.J.). When OD600 nm reached 0.6-0.8, 100 mM ZnSO$_4$ stock was added to each liter of culture to reach a final concentration of 0.1 mM. When OD reached 0.8-1.0, cultures were removed from incubator and chilled in 4° C. for 1 h. Protein expression was then induced with 0.5 mM isopropyl I3-D-1-thiogalactopyranoside (IPTG) for overnight at 16° C. Cells were harvested by centrifugation at 4,550 g (Beckman J6B Centrifuge, JS-4.2 rotor), resuspended in equilibrium buffer (25 mM HEPES pH 8.0, 500 mM NaCl, 1 mM PMSF), and lysed using a French Press (GlenMills, N.J.) at 25,000 psi for three cycles. Cell debris was removed by centrifugation at 27,000 g for 100 min (Beckman Coulter centrifuge, JA-17 rotor) and supernatants were filtered through 0.45 μm membranes.

The filtrate was loaded on a gravity flow column packed with 5 mL Ni-NTA agarose resin (Thermo Fisher Scientific, Waltham, Mass.), followed by washing with 50 mL of low-salt wash buffer (25 mM HEPES pH 8.0, 500 mM NaCl, 20 mM imidazole), 50 mL of high-salt wash buffer (25 mM HEPES pH 8.0, 1 M NaCl, 20 mM imidazole) and 50 mL of low-salt wash buffer. Proteins were then eluted with 25 mL elution buffer (25 mM HEPES pH 8.0, 500 mM NaCl, 400 mM imidazole). 25 mL no-salt buffer (50 mM Tris pH 7.0, 1 mM EDTA, 0.1 mM DTT) was then added to the eluted proteins and the proteins were loaded onto a 5-mL HiTrap Heparin HP Column by a low-pressure peristaltic pump at a flow rate of at 3 mL/min (GE Healthcare, Princeton, N.J.). Heparin column was placed on an ÄKTA Pure chromatography system to elute PARP1 using a gradient of 0-100% buffer B (50 mM Tris pH 7.0, 1 mM EDTA, 0.1 mM DTT, 1 M NaCl) in buffer A (50 mM Tris pH 7.0, 1 mM EDTA, 0.1 mM DTT, and 250 mM NaCl) at a flow rate of 1 ml/min. PARP1 was eluted starting at 40% buffer B and the collected fractions were combined and spun down to 500 μL using Amicon centrifugal filters with 30 kDa cutoff (EMD Millipore, Temecula, Calif.). The concentrated proteins were injected on to a size-exclusion chromatography column Superdex 200 Increase 10/300 GL (GE Healthcare, Princeton, N.J.) and eluted using gel filtration buffer (25 mM HEPES, pH 8.0, 150 mM NaCl, 1 mM EDTA, 0.1 mM DTT). Purified PARP1 was examined by SDS-PAGE and a NanoDrop 2000C spectrophotometer (Thermo Fisher Scientific, Waltham, Mass.), then aliquoted and flash-frozen in liquid nitrogen for storage at −80° C. Calculated molecular extinction coefficient value for human PARP1 with a C-terminal His$_6$-tag (SEQ ID NO: 3) is 1.052.

Automodification and Immunoblotting Activity Analysis. Auto-PARylation of purified PARP1 was performed at 30° C. for 2 hours in 50 μL assay solutions containing 30 mM HEPES, pH 8.0, 5 mM MgCl$_2$, 5 mM CaCl$_2$, 1 mM DTT, 100 ng/μL activated DNA, 250 μM NAD$^+$ or NAD$^+$ analogues, and 5 μM purified PARP1 or PARP1 mutant enzyme. 20 μL of the reaction was taken out and saved for SDS-PAGE analysis. The remaining reaction mixtures were further labeled with azide-biotin (for 1-4) or phosphine-PEG3-Biotin (for 5 and 6) through copper(I)-catalyzed azide alkyne cycloaddition (CuAAC) and Staudinger reaction. The CuAAC reactions were performed for one hours at room temperature in 40 μL volume, which contain 30 μL PARP1 automodification mixtures, 2 mM THPTA, 1 mM CuSO$_4$, 100 μM azide-biotin, and 10 mM sodium ascorbate in PBS. The Staudinger reactions were performed for two hours at 30° C. in 35 μL volume, which contain 30 μL PARP1 automodification mixtures and 35 μM of phosphine-PEG3-biotin. The levels of auto-PARylation were evaluated by immunoblots using a streptavidin-HRP conjugate for detection of the biotinylated PARP1 via click chemistry and Staudinger reaction.

High-performance Liquid Chromatography (HPLC)-based Kinetic Assays. Auto-PARylation of PARP1 was carried out in 80 μL assay solutions (30 mM HEPES, pH 8.0, 5 mM MgCl$_2$, 5 mM CaCl$_2$, 1 mM DTT, 100 ng/μL of activated DNA, 100 ng/μL BSA) containing varied concentrations of NAD$^+$ (50, 100, 250, 450, 600, and 750 μM) or NAD$^+$ analogues (2, 6; see Table 1) at 30° C. with purified PARP1 enzymes. The reactions were quenched at different time points (NAD$^+$: 0, 2.5, 5, 10, 15, and 20 min; 2: 0, 60, 120, 180, 240, and 300 min; 6: 0, 5, 10, 15, 20 and 30 min) using 20% ice-cold TCA. After centrifugation, the reaction mixtures were analyzed by reverse phase HPLC using a semipreparative C18 Kinetex column (5 µm, 100 Å, 150× 10.0 mm, from Phenomenex Inc, Torrance, Calif.) (mobile phase A: 0.1% formic acid (aq); mobile phase B: 0.1% formic acid in acetonitrile; flow rate=2.0 ml/min; 0-8 min: 0% B, 8-12 min: 0-50% B, 12-13 min: 50-2.5% B, 13-18 min: 2.5-40% B, 18-20 min: 40-0% B) with detection of UV absorbance at 260 nm. The retention times for NAD$^+$, 2, and 6 were 13.0, 13.6, 13.6 min, while for ADPr, ADPr 2, ADPr 6, the retention times were 6.3 min, 12.9 min, 9.0 min Standard curves for NAD$^+$ and NAD$^+$ analogues together with ADPr and ADPr analogues were constructed by linear correlations of concentrations and corresponding integrated peak areas. NADase reaction rates were determined based on the increase in peak areas of the assigned peaks of ADPr and ADPr analogues, while reaction rates for PARP activities were measured based on the decrease in peak areas of the assigned peaks of NAD$^+$ and NAD$^+$ analogues excluding NADase activity. Kinetic parameters were determined by fitting data to the Michaelis-Menten model implemented in GraphPad Prism (La Jolla, Calif.).

PARP1 is known for its ability to undergo rapid automodification in the presence of NAD$^+$ and DNA fragments. A panel of NAD$^+$ analogues with terminal alkyne or azide modifications were first screened with wild type PARP1 to test for PARylation activity through click-chemistry based immunoblots. Wild type PARP1 reactions with NAD$^+$ were used as negative controls since ADPr without clickable moieties will be inactive for conjugating with clickable biotin thus is not recognizable by the streptavidin antibody. It was shown that out of the initial compounds tested, PARP1 can use both NAD2 and NAD6 as a substrate (Table 1), resulting in strong signal as evidence for automodification. Next, it was determined that this activity was truly originated from PARP1 catalysis and not due to NAD$^+$ analogue hydrolysis by incorporating two commercially available PARP1 inhibitors, olaparib and veliparib. The catalytic activity of PARP1 can be potently suppressed by the inhibitors and the automodification signal was significantly reduced comparing with the no-inhibitor controls, confirming that NAD2 and NAD6 can actively be recognized by wild type PARP1 for use as a co-substrate. Without the clickable moieties on NAD$^+$ molecules, no automodification signals were observed for NAD$^+$-modified PARP1 on this biotinylation-based immunoblot.

After confirmation that NAD2 and 6 may be efficiently used by PARP1 for automodification as co-substrates, the enzyme kinetics of wild type PARP1 with NAD2 and 6 in comparison with NAD$^+$ were characterized. An HPLC-based method was used to measure the catalysis activity as well as the NAD$^+$ hydrolysis activity that PARP1 processes. PARP1-catalyzed automodifications were performed with NAD$^+$, NAD2, and NAD6 at various concentrations. The enzymatic reactions were quenched with ice cold TCA with a final concentration of 20% at various time points. Standard curves were created using a range of set concentrations of NAD$^+$, NAD2 and NAD6 for determination of NAD$^+$ and analogue concentration in the quenched reactions. Likewise, standard curves for ADPr, ADPr 2 and ADPr 6 were constructed and used for ADPr and analogues concentration determination. By fitting the kinetic data to Michaelis-Menten equation, the $k_{cat}$ and $K_m$ of PARP1 with NAD$^+$, NAD2 and NAD6 were calculated (Table 3).

The calculated $K_m$ for NAD$^+$ with PARP1 is 145.4±36.0 µM, consistent with the previously reported value of 97±7 µM. The $k_{cat}$ of NAD6 is 4.1±0.6 min$^{-1}$, slightly lower than that of NAD$^+$ (4.7±0.4 min$^{-1}$). The $K_m$ (370.5±104.8 µM) of NAD6 is higher than that (145.4±36 µM) of NAD$^+$. In comparison, the $k_{cat}$ of NAD2 for PARP activity is significantly lower than those of NAD$^+$ and NAD6. Same as NAD$^+$, NAD2 and NAD6 could undergo slow hydrolysis catalyzed by PARP1. Similar to their PARP activities, the NADase activity for NAD6 is comparable to that of NAD$^+$.

These results are consistent with immunoblot analyses and support NAD6 (3'-azido) and NAD2 (3'-alkyne) NAD$^+$ analogues as good substrates for PARP1-catalyzed ADP-ribosylation.

TABLE 3

Kinetic parameters of NAD$^+$, 2, and 6 for purified human full-length PARP1

|  | Substrate | $k_{cat}$ (min$^{-1}$) | $K_m$ (µM) | $k_{cat}/K_m$ (min$^{-1}$ M$^{-1}$) |
|---|---|---|---|---|
| PARP activity | NAD$^+$ | 4.7 ± 0.4 | 145.4 ± 36.0 | 3.2 × 10$^4$ |
|  | 2 | 0.06 ± 0.01 | 218.1 ± 81.7 | 2.8 × 10$^2$ |
|  | 6 | 4.1 ± 0.6 | 370.5 ± 104.8 | 1.1 × 10$^4$ |
| NADase activity | NAD$^+$ | 0.39 ± 0.08 | 471.5 ± 187.4 | 8.3 × 10$^2$ |
|  | 2 | 0.02 ± 0.01 | 661.1 ± 489.0 | 0.3 × 10$^2$ |
|  | 6 | 0.46 ± 0.17 | 326.9 ± 278.8 | 1.4 × 10$^3$ |

Example 3. Pharmaceutical Dosage Forms

The following formulations illustrate representative pharmaceutical dosage forms that may be used for the therapeutic or prophylactic administration of a composition described herein, or a composition specifically disclosed herein (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
|  | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
|  | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
|  | 600.0 |

| (iv) Injection 1 (1 mg/mL) | mg/mL |
|---|---|
| 'Composition X' (free acid form) | 1.0 |
| Dibasic sodium phosphate | 12.0 |
| Monobasic sodium phosphate | 0.7 |
| Sodium chloride | 4.5 |

| (iv) Injection 1 (1 mg/mL) | mg/mL |
|---|---|
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' (free acid form) | 10.0 |
| Monobasic sodium phosphate | 0.3 |
| Dibasic sodium phosphate | 1.1 |
| Polyethylene glycol 400 | 200.0 |
| 0.1N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

| (vii) Topical Gel 1 | wt. % |
|---|---|
| 'Composition X' | 5% |
| Carbomer 934 | 1.25% |
| Triethanolamine (pH adjustment to 5-7) | q.s. |
| Methyl paraben | 0.2% |
| Purified water | q.s. to 100 g |

| (viii) Topical Gel 2 | wt. % |
|---|---|
| 'Composition X' | 5% |
| Methylcellulose | 2% |
| Methyl paraben | 0.2% |
| Propyl paraben | 0.02% |
| Purified water | q.s. to 100 g |

| (ix) Topical Ointment | wt. % |
|---|---|
| 'Composition X' | 5% |
| Propylene glycol | 1% |
| Anhydrous ointment base | 40% |
| Polysorbate 80 | 2% |
| Methyl paraben | 0.2% |
| Purified water | q.s. to 100 g |

| (x) Topical Cream 1 | wt. % |
|---|---|
| 'Composition X' | 5% |
| White bees wax | 10% |
| Liquid paraffin | 30% |
| Benzyl alcohol | 5% |
| Purified water | q.s. to 100 g |

| (xi) Topical Cream 2 | wt. % |
|---|---|
| 'Composition X' | 5% |
| Stearic acid | 10% |
| Glyceryl monostearate | 3% |
| Polyoxyethylene stearyl ether | 3% |
| Sorbitol | 5% |
| Isopropyl palmitate | 2% |
| Methyl Paraben | 0.2% |
| Purified water | q.s. to 100 g |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, such embodiments are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. No limitations inconsistent with this disclosure are to be understood therefrom. The invention has been described with reference to various specific and preferred embodiments and techniques. However, it should be understood that many variations and modifications may be made while remaining within the spirit and scope of the invention.

What is claimed is:

1. An antibody-drug conjugate comprising:

an automodified poly ADP-ribose polymerase (PARP), wherein the automodified PARP is PARP1 or PARP2, the automodified PARP comprising a plurality of poly ADP-ribose (ADPr) polymers on a surface of the automodified PARP, wherein the poly ADPr polymers comprise one or more substituted dinucleotides according to Formula I having one or more alkyne or azido moieties:

(I)

wherein $R^1$ is $OCH_2C\equiv CH$, $O(CH_2)_3C\equiv CH$, $O(CH_2)_2N_3$, OH, or $N_3$;

$R^2$ is $OCH_2C\equiv CH$, $O(CH_2)_3C\equiv CH$, OH, or $N_3$;

$R^3$ is $CH_2C\equiv CH$ or H; and $R^4$ is $C\equiv CH$ or H;

an antibody conjugated to the automodified PARP; and
an active agent conjugated to the automodified PARP.

2. The antibody-drug conjugate of claim 1 wherein the automodified PARP is linked to the antibody through an alkyne-derived linkage, or a polyethylene glycol linking group.

3. The antibody-drug conjugate of claim 1 wherein the automodified PARP is linked to the active agent through an alkyne-derived linkage, a cyclooctyne-derived linker, or a polyethylene glycol linking group.

4. The antibody-drug conjugate of claim 1 wherein the active agent is a cytotoxic drug.

5. The antibody-drug conjugate of claim 4 wherein the cytotoxic drug is effective to treat breast cancer, multiple myeloma, or lymphoma.

6. The antibody-drug conjugate of claim 5 wherein the breast cancer is HER2-positive metastatic breast cancer.

7. The antibody-drug conjugate of claim 6 wherein the cytotoxic drug is auristatin, calicheamicin, maytansine, or a DNA alkylating agent.

8. The antibody-drug conjugate of claim 1 wherein the ratio of automodified PARP to active agent conjugated to the antibody-drug conjugate is 1:10 to about 1:100.

9. The antibody-drug conjugate of claim 1 wherein the automodified PARP is linked to at least one antibody through an alkyne-derived linkage or a first polyethylene glycol linking group, the automodified PARP is linked to at least one active agent through an alkyne-derived linkage, a cyclooctyne-derived linker, or a second polyethylene glycol linking group, and the ratio of the automodified PARP to active agent conjugated to the antibody-drug conjugate is 1:10 to about 1:100.

10. The antibody-drug conjugate of claim 9 wherein the automodified PARP is linked to the antibody through an alkyne-derived linkage, the automodified PARP is linked to the active agent through an alkyne-derived linkage or a cyclooctyne-derived linker, the antibody comprises trastuzumab, and the active agent is monomethyl auristatin F or monomethyl auristatin-E.

11. The antibody-drug conjugate of claim 1 wherein $R^1$, $R^2$, $R^3$, and $R^4$ of the substituted dinucleotide of Formula I are defined as one of (a) to (i):
   a. $R^1$ is $OCH_2C\equiv CH$, $R^2$ is OH, $R^3$ is H, and $R^4$ is H;
   b. $R^1$ is OH, $R^2$ is $OCH_2C\equiv CH$, $R^3$ is H, and $R^4$ is H;
   c. $R^1$ is $O(CH_2)_3C\equiv CH$, —$R^2$— is OH, $R^3$ is H, and $R^4$ is H;
   d. $R^1$ is OH, $R^2$ is $O(CH_2)_3C\equiv CH$, $R^3$ is H, and $R^4$ is H;
   e. $R^1$ is $N_3$, $R^2$ is OH, $R^3$ is H, and $R^4$ is H;
   f. $R^1$ is OH, $R^2$ is $N_3$, $R^3$ is H, and $R^4$ is H;
   g. $R^1$ is $O(CH_2)_2N_3$, $R^2$ is OH, $R^3$ is H, and $R^4$ is H;
   h. $R^1$ is OH, $R^2$ is OH, $R^3$ is $CH_2C\equiv CH$, and $R^4$ is H; or
   i. $R^1$ is OH, $R^2$ is OH, $R^3$ is H, and $R^4$ is $C\equiv CH$.

12. The antibody-drug conjugate of claim 1 wherein
   $R^1$ is $O(CH_2)_2N_3$, OH, or $N_3$;
   $R^2$ is OH or $N_3$; and
   $R^3$ and $R^4$ are H;
with the proviso that if $R^1$ is $O(CH_2)_2N_3$ or $N_3$, then $R^2$ is OH; or if $R^2$ is $N_3$, then $R^1$ is OH.

13. A method of treating cancer comprising administering to a subject having cancer a therapeutically effective amount of the antibody-drug conjugate of claim 1, thereby inhibiting the growth of cancer cells or killing cancer cells.

14. The method of claim 13 wherein the ratio of automodified PARP to active agent in the antibody-drug conjugate is about 1 to about 20, about 1 to about 50, or about 1 to about 100.

15. The method of claim 13 wherein the cancer is breast cancer, multiple myeloma, or lymphoma.

16. The method of claim 13 wherein the automodified PARP is linked to at least one antibody through an alkyne-derived linkage or a first polyethylene glycol linking group, the automodified PARP is linked to at least one active agent through an alkyne-derived linkage, a cyclooctyne-derived linker, or a second polyethylene glycol linking group, and the ratio of automodified PARP to active agent conjugated to the antibody-drug conjugate is 1:10 to about 1:100, or
   wherein the automodified PARP is linked to the antibody through an alkyne-derived linkage, the automodified PARP is linked to the active agent through an alkyne-derived linkage or a cyclooctyne-derived linker, the antibody comprises trastuzumab, and the active agent is monomethyl auristatin F or monomethyl auristatin-E.

17. A method of preparing an antibody-drug conjugate comprising:
   combining a linker and a antibody to provide an antibody-linker conjugate;
   combining PARP1 or PARP2 and a substituted dinucleotide to provide an automodified PARP comprising a plurality of poly ADP-ribose (ADPr) polymers on a surface of the automodified PARP, wherein the substituted dinucleotide is one or more substituted dinucleotides according to Formula I having one or more alkyne or azido groups:

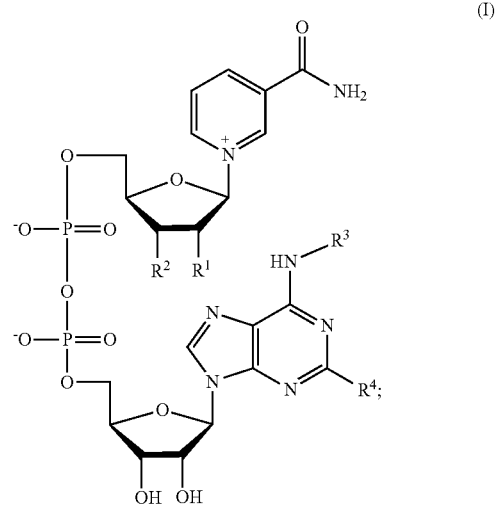

wherein $R^1$ is $OCH_2C\equiv CH$, $O(CH_2)_3C\equiv CH$, $O(CH_2)_2N_3$, OH, or $N_3$;
$R^2$ is $OCH_2C\equiv CH$, $O(CH_2)_3C\equiv CH$, OH, or $N_3$;
$R^3$ is $CH_2C\equiv CH$ or H: and
$R^4$ is $C\equiv CH$ or H; and
combining the automodified PARP, the antibody-linker conjugate, and an active agent under suitable conditions such that the antibody-linker conjugate and an active agent conjugate to the substituted dinucleotide through click chemistry to provide the antibody-drug conjugate.

18. The method of claim 17 wherein $R^1$, $R^2$, $R^3$, and $R^4$ of the substituted dinucleotide of Formula I are defined as one of (a) to (i):
   a. $R^1$ is $OCH_2C\equiv CH$, $R^2$ is OH, $R^3$ is H, and $R^4$ is H;
   b. $R^1$ is OH, $R^2$ is $OCH_2C\equiv CH$, $R^3$ is H, and $R^4$ is H;
   c. $R^1$ is $O(CH_2)_3C\equiv CH$, —$R^2$— is OH, $R^3$ is H, and $R^4$ is H;
   d. $R^1$ is OH, $R^2$ is $O(CH_2)_3C\equiv CH$, $R^3$ is H, and $R^4$ is H;
   e. $R^1$ is $N_3$, $R^2$ is OH, $R^3$ is H, and $R^4$ is H;
   f. $R^1$ is OH, $R^2$ is $N_3$, $R^3$ is H, and $R^4$ is H;
   g. $R^1$ is $O(CH_2)_2N_3$, $R^2$ is OH, $R^3$ is H, and $R^4$ is H;
   h. $R^1$ is OH, $R^2$ is OH, $R^3$ is $CH_2C\equiv CH$, and $R^4$ is H; or
   i. $R^1$ is OH, $R^2$ is OH, $R^3$ is H, and $R^4$ is $C\equiv CH$.

19. The method of claim 17 wherein the ratio of automodified PARP to active agent in the composition is about 1 to about 20, about 1 to about 50, or about 1 to about 100.

* * * * *

SEQUENCE LISTING

<160> NUMBER OF SEQ ID NOS: 3

<210> SEQ ID NO 1
<211> LENGTH: 42
<212> TYPE: DNA
<213> ORGANISM: Artificial Sequence
<220> FEATURE:
<223> OTHER INFORMATION: Description of Artificial Sequence: Synthetic primer

<400> SEQUENCE: 1

```
tggtgctcga gccacaggga ggtcttaaaa ttgaatttca gt                          42

<210> SEQ ID NO 2
<211> LENGTH: 66
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
ccctctagaa ataattttgt ttaactttaa gaaggagata taccatggcg gagtcttcgg       60
ataagc                                                                 66

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 3

His His His His His His
1               5
```